(12) United States Patent
Khamis et al.

(10) Patent No.: US 9,333,065 B2
(45) Date of Patent: *May 10, 2016

(54) PELVIC FLOOR TREATMENTS AND RELATED TOOLS AND IMPLANTS

(71) Applicant: AMS Research Corporation, Minnetonka, MN (US)

(72) Inventors: Chaouki A. Khamis, Edina, MN (US); David J. Kupiecki, Edina, MN (US); Jeffrey M. O'Hern, Golden Valley, MN (US); Shawn Michael Wignall, Woodbury, MN (US)

(73) Assignee: Astora Women's Health, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/263,184

(22) Filed: Apr. 28, 2014

(65) Prior Publication Data

US 2014/0235935 A1    Aug. 21, 2014

Related U.S. Application Data

(63) Continuation of application No. 12/678,923, filed as application No. PCT/US2008/010926 on Sep. 19, 2008, now Pat. No. 8,708,885.

(60) Provisional application No. 60/974,314, filed on Sep. 21, 2007, provisional application No. 61/012,260, filed on Dec. 7, 2007.

(51) Int. Cl.
*A61F 2/00* (2006.01)
*A61B 17/00* (2006.01)
(Continued)

(52) U.S. Cl.
CPC .......... *A61F 2/0063* (2013.01); *A61B 17/00234* (2013.01); *A61B 17/0401* (2013.01);
(Continued)

(58) Field of Classification Search
CPC ................... A61B 17/00234; A61B 17/0401; A61B 17/3468; A61B 2017/00805; A61B 2017/0409; A61B 2017/0412; A61B 2017/0464; A61B 19/4805; A61B 2019/481; A61B 17/0427; A61F 2002/0072; A61F 2/0045; A61F 2/0063
See application file for complete search history.

(56) References Cited

U.S. PATENT DOCUMENTS 4,632,100 A    12/1986    Somers et al.
4,932,962 A    6/1990    Yoon et al.
(Continued)

FOREIGN PATENT DOCUMENTS

AU    2002241673    11/2005
CA    2404459    8/2005
(Continued)

OTHER PUBLICATIONS

"We're staying ahead of the curve" Introducing the IVS Tunneller Device for Tension Free Procedures, Tyco Healthcare, 3 pages (2002).
(Continued)

*Primary Examiner* — Charles A Marmor, II
*Assistant Examiner* — Joshua D Lannu
(74) *Attorney, Agent, or Firm* — Kagan Binder, PLLC

(57) ABSTRACT

Described are implants, tools, and methods useful for treating pelvic conditions such as prolapse, by placing an implant to support pelvic tissue, the implants, tools, and methods involving one or more of an insertion tool that works in coordination with a sheath, adjusting engagements, specific implants and pieces of implants, placement of implants at locations within the pelvic region, and insertion, adjusting, and grommet management tools.

16 Claims, 10 Drawing Sheets

(51) Int. Cl.
*A61B 17/04* (2006.01)
*A61B 17/34* (2006.01)
*A61B 19/00* (2006.01)

(52) U.S. Cl.
CPC ........... *A61F 2/0045* (2013.01); *A61B 17/3468* (2013.01); *A61B 2017/00805* (2013.01); *A61B 2017/0409* (2013.01); *A61B 2017/0412* (2013.01); *A61B 2017/0427* (2013.01); *A61B 2017/0464* (2013.01); *A61B 2019/481* (2013.01); *A61B 2019/4805* (2013.01); *A61F 2002/0072* (2013.01)

(56) References Cited

U.S. PATENT DOCUMENTS

| | | | |
|---|---|---|---|
| 5,013,292 A | 5/1991 | Lemay | |
| 5,013,316 A | 5/1991 | Goble et al. | |
| 5,053,043 A | 10/1991 | Gottesman et al. | |
| 5,085,661 A | 2/1992 | Moss | |
| 5,112,344 A | 5/1992 | Petros | |
| 5,149,329 A | 9/1992 | Richardson | |
| 5,152,749 A * | 10/1992 | Giesy et al. | 604/164.01 |
| 5,188,636 A | 2/1993 | Fedotov | |
| 5,203,864 A | 4/1993 | Phillips | |
| 5,234,438 A | 8/1993 | Semrad | |
| 5,256,133 A | 10/1993 | Spitz | |
| 5,268,001 A | 12/1993 | Nicholson et al. | |
| 5,281,237 A | 1/1994 | Gimpelson | |
| 5,328,077 A | 7/1994 | Lou | |
| 5,337,736 A | 8/1994 | Reddy | |
| 5,354,292 A | 10/1994 | Braeuer et al. | |
| 5,368,595 A | 11/1994 | Lewis | |
| 5,370,650 A | 12/1994 | Tovey et al. | |
| 5,376,097 A | 12/1994 | Phillips | |
| 5,403,328 A | 4/1995 | Shallman | |
| 5,439,467 A | 8/1995 | Benderev et al. | |
| 5,474,518 A | 12/1995 | Velaquez | |
| 5,474,543 A | 12/1995 | McKay | |
| 5,520,700 A | 5/1996 | Beyar et al. | |
| 5,520,703 A | 5/1996 | Essig | |
| 5,527,342 A | 6/1996 | Pietrzak et al. | |
| 5,544,664 A | 8/1996 | Benderev et al. | |
| 5,562,689 A | 10/1996 | Green et al. | |
| 5,582,188 A | 12/1996 | Benderev et al. | |
| 5,584,860 A | 12/1996 | Goble et al. | |
| 5,591,163 A | 1/1997 | Thompson | |
| 5,591,206 A | 1/1997 | Moufarrege | |
| 5,611,515 A | 3/1997 | Benderev et al. | |
| 5,674,247 A | 10/1997 | Sohn | |
| 5,683,349 A | 11/1997 | Makower et al. | |
| 5,690,655 A | 11/1997 | Hart et al. | |
| 5,697,931 A | 12/1997 | Thompson | |
| 5,725,529 A | 3/1998 | Nicholson et al. | |
| 5,725,541 A | 3/1998 | Anspach, III et al. | |
| 5,741,282 A | 4/1998 | Anspach, III et al. | |
| 5,782,862 A | 7/1998 | Bonuttie | |
| 5,873,891 A | 2/1999 | Sohn | |
| 5,899,909 A | 5/1999 | Claren et al. | |
| 5,944,732 A | 8/1999 | Raulerson et al. | |
| 5,954,057 A | 9/1999 | Li | |
| 5,972,000 A | 10/1999 | Beyar et al. | |
| 5,980,558 A | 11/1999 | Wiley | |
| 5,997,554 A | 12/1999 | Thompson | |
| 6,030,393 A | 2/2000 | Corlew | |
| 6,042,583 A | 3/2000 | Thompson et al. | |
| 6,048,351 A | 4/2000 | Gordon et al. | |
| 6,053,935 A | 4/2000 | Brenneman et al. | |
| 6,056,688 A | 5/2000 | Benderev et al. | |
| 6,099,538 A | 8/2000 | Moses | |
| 6,099,551 A | 8/2000 | Gabby | |
| 6,168,611 B1 | 1/2001 | Risvi | |
| 6,241,736 B1 | 6/2001 | Sater et al. | |
| 6,245,082 B1 | 6/2001 | Gellman et al. | |
| 6,264,676 B1 | 7/2001 | Gellman et al. | |
| 6,273,852 B1 | 8/2001 | Lehe et al. | |
| 6,319,272 B1 | 11/2001 | Brenneman et al. | |
| 6,322,492 B1 | 11/2001 | Kovac | |
| 6,328,744 B1 | 12/2001 | Harari et al. | |
| 6,334,446 B1 | 1/2002 | Beyar | |
| 6,382,214 B1 | 5/2002 | Raz et al. | |
| 6,406,423 B1 | 6/2002 | Scetbon | |
| 6,406,480 B1 | 6/2002 | Beyar et al. | |
| 6,423,072 B1 | 7/2002 | Zappala | |
| 6,423,080 B1 | 7/2002 | Gellman et al. | |
| 6,440,154 B2 | 8/2002 | Gellman et al. | |
| 6,451,024 B1 | 9/2002 | Thompson et al. | |
| 6,454,778 B2 | 9/2002 | Kortenbach | |
| 6,475,139 B1 | 11/2002 | Miller | |
| 6,478,727 B2 | 11/2002 | Scetbon | |
| 6,491,703 B1 | 12/2002 | Ulmsten | |
| 6,502,578 B2 | 1/2003 | Raz et al. | |
| 6,506,190 B1 | 1/2003 | Walshe | |
| 6,530,943 B1 | 3/2003 | Hoepffner et al. | |
| 6,544,273 B1 | 4/2003 | Harari et al. | |
| 6,592,515 B2 | 7/2003 | Thierfelder | |
| 6,592,610 B2 | 7/2003 | Beyar | |
| 6,596,001 B2 | 7/2003 | Stormby et al. | |
| 6,599,235 B2 | 7/2003 | Kovac | |
| 6,602,260 B2 | 8/2003 | Harari et al. | |
| 6,612,977 B2 | 9/2003 | Staskin | |
| 6,635,058 B2 | 10/2003 | Beyar et al. | |
| 6,638,210 B2 | 10/2003 | Berger | |
| 6,641,525 B2 | 11/2003 | Rocheleau | |
| 6,652,450 B2 | 11/2003 | Neisz et al. | |
| 6,673,010 B2 | 1/2004 | Skiba et al. | |
| 6,685,629 B2 | 2/2004 | Therin | |
| 6,689,047 B2 | 2/2004 | Gellman et al. | |
| 6,702,827 B1 | 3/2004 | Lund | |
| 6,730,110 B1 | 5/2004 | Harari et al. | |
| 6,746,455 B2 | 6/2004 | Beyar et al. | |
| 6,752,814 B2 | 6/2004 | Gellman et al. | |
| 6,802,807 B2 | 10/2004 | Anderson | |
| 6,884,212 B2 | 4/2005 | Thierfelder et al. | |
| 6,908,425 B2 | 6/2005 | Luscombe | |
| 6,908,473 B2 | 6/2005 | Skiba et al. | |
| 6,911,003 B2 | 6/2005 | Anderson et al. | |
| 6,932,759 B2 | 8/2005 | Kammerer | |
| 6,936,052 B2 | 8/2005 | Gellman et al. | |
| 6,971,986 B2 | 12/2005 | Staskin et al. | |
| 6,991,597 B2 | 1/2006 | Gellman et al. | |
| 7,014,607 B2 | 3/2006 | Gellman | |
| 7,025,772 B2 | 4/2006 | Gellman et al. | |
| 7,037,255 B2 | 5/2006 | Inman | |
| 7,048,682 B2 | 5/2006 | Neisz et al. | |
| 7,070,556 B2 | 7/2006 | Anderson et al. | |
| 7,083,637 B1 | 8/2006 | Tannhauser | |
| 7,087,059 B2 | 8/2006 | Harari et al. | |
| 7,112,171 B2 | 9/2006 | Rocheleau et al. | |
| 7,121,997 B2 | 10/2006 | Kammerer et al. | |
| 7,131,943 B2 | 11/2006 | Kammerer | |
| 7,223,229 B2 | 5/2007 | Inman et al. | |
| 7,226,407 B2 | 6/2007 | Kammerer | |
| 7,226,408 B2 | 6/2007 | Harari et al. | |
| 7,229,404 B2 | 6/2007 | Bouffier | |
| 7,229,453 B2 | 6/2007 | Anderson | |
| 7,235,043 B2 | 6/2007 | Gellman et al. | |
| 7,261,723 B2 | 8/2007 | Smith et al. | |
| 7,267,645 B2 | 9/2007 | Anderson et al. | |
| 7,291,104 B2 | 11/2007 | Neisz et al. | |
| 7,297,102 B2 | 11/2007 | Smith et al. | |
| 7,303,525 B2 | 12/2007 | Watschke et al. | |
| 7,347,812 B2 | 3/2008 | Mellier | |
| 7,351,196 B2 | 4/2008 | Goldmann et al. | |
| 7,351,197 B2 | 4/2008 | Montpetit et al. | |
| 7,357,773 B2 | 4/2008 | Watschke et al. | |
| 7,364,541 B2 | 4/2008 | Chu et al. | |
| 7,371,245 B2 | 5/2008 | Evans et al. | |
| 7,387,634 B2 | 6/2008 | Benderev | |
| 7,393,320 B2 | 7/2008 | Montpetit et al. | |
| 7,407,480 B2 | 8/2008 | Staskin et al. | |
| 7,410,460 B2 | 8/2008 | Benderev | |
| 7,413,540 B2 | 8/2008 | Gellman et al. | |
| 7,422,557 B2 | 9/2008 | Arnal | |

(56) References Cited

U.S. PATENT DOCUMENTS

| | | |
|---|---|---|
| 7,494,495 B2 | 2/2009 | Delorme et al. |
| 7,500,945 B2 | 3/2009 | Cox |
| 7,517,313 B2 | 4/2009 | Thierfelder et al. |
| 7,527,588 B2 | 5/2009 | Zaddem et al. |
| 7,527,633 B2 | 5/2009 | Rioux |
| 7,547,316 B2 | 6/2009 | Rioux |
| 7,588,598 B2 | 9/2009 | Delorme et al. |
| 7,601,118 B2 | 10/2009 | Smith et al. |
| 7,614,999 B2 | 11/2009 | Gellman et al. |
| 7,621,865 B2 | 11/2009 | Gellman et al. |
| 7,637,860 B2 | 12/2009 | MacLean |
| 7,686,759 B2 | 3/2010 | Sater |
| 7,686,760 B2 | 3/2010 | Anderson et al. |
| 7,691,050 B2 | 4/2010 | Gellman et al. |
| 7,691,052 B2 | 4/2010 | Gellman et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,828,715 B2 | 11/2010 | Haverfield |
| 7,905,825 B2 | 3/2011 | Arnal et al. |
| 7,909,753 B1 | 3/2011 | Ogdahl et al. |
| 7,914,437 B2 | 3/2011 | Gozzi |
| 2001/0000533 A1 | 4/2001 | Kovac |
| 2001/0018549 A1 | 8/2001 | Scetbon |
| 2001/0027321 A1 | 10/2001 | Gellman et al. |
| 2001/0041895 A1 | 11/2001 | Beyer et al. |
| 2001/0049467 A1 | 12/2001 | Lehe et al. |
| 2001/0053916 A1 | 12/2001 | Rioux |
| 2002/0007222 A1 | 1/2002 | Desai |
| 2002/0028980 A1 | 3/2002 | Thierfelder et al. |
| 2002/0035369 A1 | 3/2002 | Beyar et al. |
| 2002/0038119 A1 | 3/2002 | Weber et al. |
| 2002/0038132 A1 | 3/2002 | Abrams |
| 2002/0050277 A1 | 5/2002 | Beyar |
| 2002/0055748 A1 | 5/2002 | Gellman et al. |
| 2002/0058959 A1 | 5/2002 | Gellman et al. |
| 2002/0068948 A1 | 6/2002 | Stormby et al. |
| 2002/0077526 A1 | 6/2002 | Kammerer et al. |
| 2002/0091373 A1 | 7/2002 | Berger |
| 2002/0095064 A1 | 7/2002 | Beyar |
| 2002/0095163 A1 | 7/2002 | Beyer et al. |
| 2002/0095181 A1 | 7/2002 | Beyar |
| 2002/0107525 A1 | 8/2002 | harari et al. |
| 2002/0128681 A1 | 9/2002 | Broome et al. |
| 2002/0147382 A1 | 10/2002 | Neisz et al. |
| 2002/0151909 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065402 A1 | 4/2003 | Anderson et al. |
| 2003/0171644 A1 | 9/2003 | Anderson et al. |
| 2003/0176875 A1 | 9/2003 | Anderson |
| 2003/0212305 A1 | 11/2003 | Anderson et al. |
| 2003/0225424 A1 | 12/2003 | Benderev |
| 2004/0015057 A1 | 1/2004 | Rocheleau et al. |
| 2004/0039453 A1 | 2/2004 | Anderson et al. |
| 2004/0087970 A1 | 5/2004 | Chu et al. |
| 2004/0193215 A1 | 9/2004 | Harari et al. |
| 2004/0225181 A1 | 11/2004 | Chu et al. |
| 2004/0267088 A1 | 12/2004 | Kammerer |
| 2005/0000523 A1 | 1/2005 | Beraud |
| 2005/0004426 A1 | 1/2005 | Raz et al. |
| 2005/0004576 A1 | 1/2005 | Benderev |
| 2005/0131391 A1* | 6/2005 | Chu et al. ............ 606/1 |
| 2005/0131393 A1 | 6/2005 | Chu et al. |
| 2005/0199249 A1 | 9/2005 | Karram |
| 2005/0245787 A1 | 11/2005 | Cox et al. |
| 2005/0250977 A1 | 11/2005 | Montpetit et al. |
| 2005/0256366 A1 | 11/2005 | Chu |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0195007 A1 | 8/2006 | Anderson |
| 2006/0195010 A1 | 8/2006 | Arnal et al. |
| 2006/0195011 A1 | 8/2006 | Arnal |
| 2006/0217589 A1 | 9/2006 | Wam et al. |
| 2006/0229493 A1 | 10/2006 | Weiser et al. |
| 2006/0229596 A1 | 10/2006 | Weiser et al. |
| 2006/0235262 A1 | 10/2006 | Arnal et al. |
| 2006/0260618 A1 | 11/2006 | Hodroff et al. |
| 2006/0287571 A1 | 12/2006 | Gozzi |
| 2007/0010830 A1 | 1/2007 | Gellman et al. |
| 2007/0015953 A1 | 1/2007 | MacLean |
| 2007/0078295 A1 | 4/2007 | landgrebe |
| 2007/0173864 A1 | 7/2007 | Chu |
| 2008/0039678 A1 | 2/2008 | Montpetit et al. |
| 2008/0082105 A1 | 4/2008 | Chu |
| 2008/0103351 A1 | 5/2008 | Montpetit et al. |
| 2008/0140218 A1 | 6/2008 | Staskin et al. |
| 2008/0207989 A1 | 8/2008 | Kaleta et al. |
| 2008/0300607 A1 | 12/2008 | Meade et al. |
| 2009/0012592 A1 | 1/2009 | Ogdahl et al. |
| 2009/0137864 A1 | 5/2009 | Cox et al. |
| 2009/0156891 A1 | 6/2009 | Heys et al. |
| 2009/0182190 A1 | 7/2009 | Dann |
| 2009/0221867 A1 | 9/2009 | Ogdahl et al. |
| 2009/0221868 A1 | 9/2009 | Evans |
| 2009/0240104 A1 | 9/2009 | Ogdahl et al. |
| 2010/0105979 A1 | 4/2010 | Otte et al. |
| 2010/0152528 A1 | 6/2010 | Chapmenan et al. |
| 2010/0168505 A1 | 7/2010 | Inman et al. |
| 2010/0256442 A1 | 10/2010 | Ogdahl et al. |
| 2010/0261952 A1 | 10/2010 | Montpetit et al. |
| 2011/0034759 A1 | 2/2011 | Ogdahl et al. |
| 2011/0082328 A1 | 4/2011 | Gozzi et al. |

FOREIGN PATENT DOCUMENTS

| | | |
|---|---|---|
| DE | 2305815 | 2/1973 |
| DE | 4220283 C2 | 5/1994 |
| DE | 10211360 | 9/2003 |
| DE | 20016866 | 3/2007 |
| EP | 0650703 A1 | 6/1994 |
| EP | 0643945 A2 | 7/1994 |
| EP | 1093758 A1 | 4/2001 |
| EP | 1342450 B1 | 9/2003 |
| FR | 2852813 A1 | 1/2004 |
| FR | 285217 | 10/2004 |
| GB | 2268690 A | 1/1994 |
| GB | 2353220 A | 10/2000 |
| SU | 1225547 A1 | 4/1986 |
| SU | 1342486 A | 10/1987 |
| WO | WO9310715 A1 | 6/1993 |
| WO | WO9319678 A2 | 10/1993 |
| WO | WO9716121 A1 | 5/1997 |
| WO | WO97306338 A1 | 8/1997 |
| WO | WO9747244 A1 | 12/1997 |
| WO | WO9846142 A1 | 4/1998 |
| WO | WO9819606 A1 | 5/1998 |
| WO | WO9835606 A1 | 8/1998 |
| WO | WO9835616 A1 | 8/1998 |
| WO | WO 9846142 A1 * | 10/1998 |
| WO | WO9937216 A1 | 7/1999 |
| WO | WO9937217 A1 | 7/1999 |
| WO | WO9958074 A2 | 11/1999 |
| WO | WO9959477 A1 | 11/1999 |
| WO | WO0030556 A1 | 6/2000 |
| WO | WO0040158 A2 | 7/2000 |
| WO | WO0057796 A1 | 10/2000 |
| WO | WO0074594 A1 | 12/2000 |

(56) References Cited

FOREIGN PATENT DOCUMENTS

| | | |
|---|---|---|
| WO | WO0074613 A1 | 12/2000 |
| WO | WO0074633 A2 | 12/2000 |
| WO | WO0232284 A2 | 4/2002 |
| WO | WO02302934 A1 | 4/2002 |
| WO | WO0234124 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO03013392 A2 | 2/2003 |
| WO | WO03017848 A1 | 3/2003 |
| WO | WO03034891 A2 | 5/2003 |
| WO | WO03034939 A1 | 5/2003 |
| WO | WO03047435 A1 | 6/2003 |
| WO | WO03068107 A1 | 8/2003 |
| WO | WO03075792 A1 | 9/2003 |
| WO | WO03086205 A2 | 10/2003 |
| WO | WO03092546 A2 | 11/2003 |
| WO | WO03096928 A1 | 11/2003 |
| WO | WO03096929 A1 | 11/2003 |
| WO | WO2004012579 A2 | 2/2004 |
| WO | WO2004016196 A2 | 2/2004 |
| WO | WO2004034912 A1 | 4/2004 |
| WO | WO2005046511 A2 | 5/2005 |
| WO | WO2005048850 A2 | 6/2005 |
| WO | WO2005079702 A1 | 9/2005 |
| WO | WO2005122954 A1 | 12/2005 |
| WO | WO2006007189 A1 | 1/2006 |
| WO | WO2006007190 A1 | 1/2006 |
| WO | WO2006031879 A1 | 3/2006 |
| WO | WO2006069078 | 6/2006 |
| WO | WO 2006108145 A1 * | 10/2006 |
| WO | WO2006108145 A1 | 10/2006 |
| WO | WO2007014241 A1 | 2/2007 |
| WO | WO2007016083 A1 | 2/2007 |
| WO | WO2007016698 A1 | 2/2007 |
| WO | WO2007027592 A2 | 3/2007 |
| WO | WO2007059199 A2 | 5/2007 |
| WO | WO 2007059199 A2 * | 5/2007 |
| WO | WO2007059306 | 5/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149593 | 12/2007 |
| WO | WO2008013867 A1 | 1/2008 |
| WO | WO2008057261 A2 | 5/2008 |
| WO | WO2008124056 A1 | 10/2008 |
| WO | WO2009005714 A2 | 1/2009 |
| WO | WO2009011852 | 1/2009 |
| WO | WO2009017680 A2 | 2/2009 |
| WO | WO2010093421 | 8/2010 |

OTHER PUBLICATIONS

Advantage A/T™, Surgical Mesh Sling Kit, Boston Scientific, 6 pages (2002).
Benderev, Theodore V., MD, A Modified Percutaneous Outpatient Bladder Neck Suspension System, Journal of Urology, vol. 152, pp. 2316-20 (Dec. 1994).
Benderev, Theodore V., MD, Anchor Fixation and Other Modifications of Endoscopic Bladder Neck Suspension, Urology, vol. 40, No. 5, pp. 409-18 (Nov. 1992).
Capio™ CL—Transvaginal Suture Capturing Device—Transvaginal Suture Fixation to Cooper's Ligament for Sling Procedures, Boston Scientific, Microvasive®, 8 pages, (2002).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Gynecare TVT Tension-Free Support for Incontinence, The tension-free solution to female Incontinence, Gynecare Worldwide,6 pages, (2002).
IVS Tunneller—A Universal instrument for anterior and posterior intra-vaginal tape placement, Tyco Healthcare, 4 pages (Aug. 2002).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
SABRE™ Bioabsorbable Sling, Generation Now, Mentor, 4 pages (May 2002).
SABRE™ Surgical Procedure, Mentor, 6 pages (Aug. 2002).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Precision Twist, Low Profile design for Precise Anchor Placement, Boston Scientific Microvasive, 2001 2 pp.
Vesica Sling Kit, Microvasive Boston Scientific, 1997, 6pp.
Precision Tack, The Precise Approach to Transvaginal Sling Procedures, Boston Scientific, 1998, 4pp.

* cited by examiner

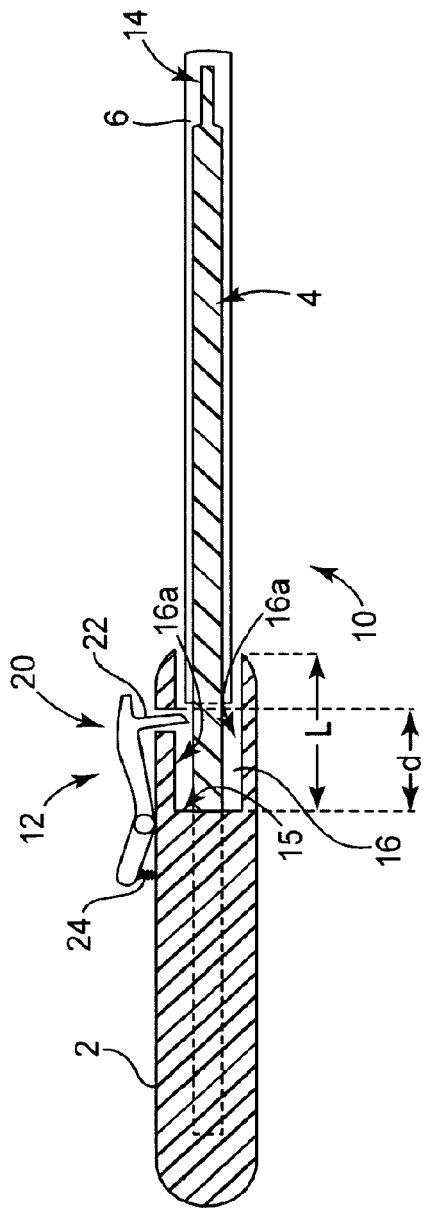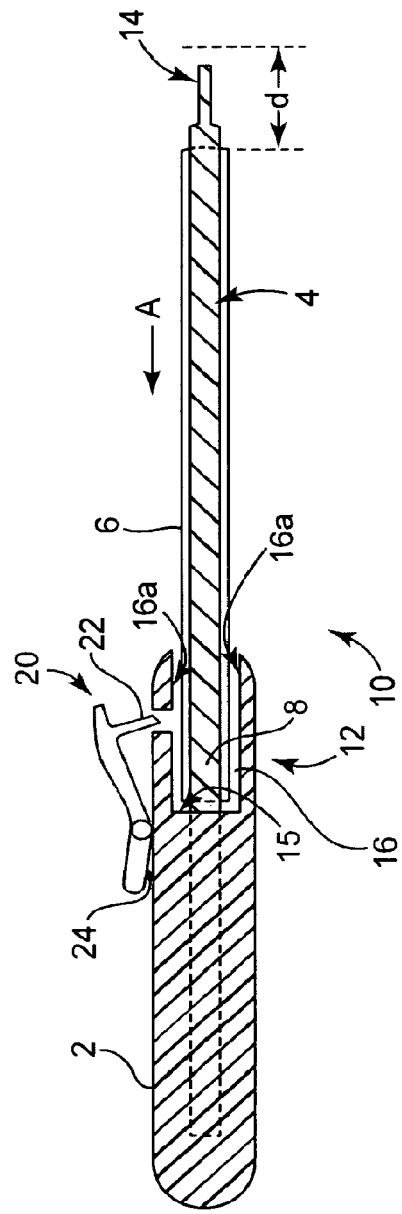

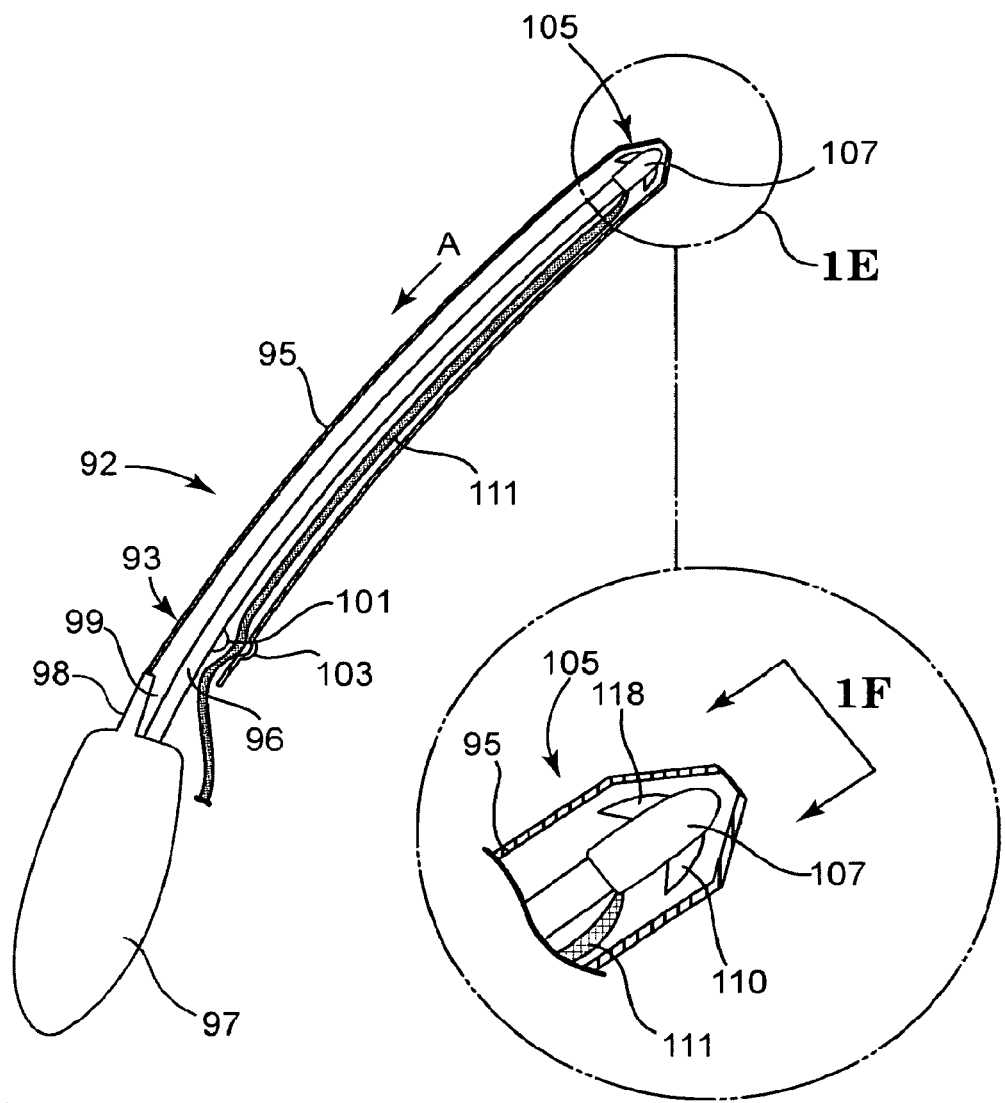
Fig. 1D
Fig. 1E
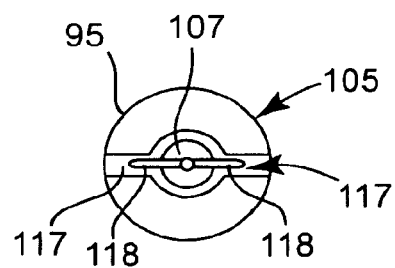
Fig. 1F

PELVIC FLOOR TREATMENTS AND RELATED TOOLS AND IMPLANTS

PRIORITY CLAIM

This application is a continuation application of U.S. patent application Ser. No. 12/678,923, filed Mar. 18, 2013, which claims benefit from International Application No. PCT/US2008/010926, which was filed on Sep. 19, 2008, which in turn claims priority to U.S. Provisional Patent Application having Ser. No. 60/974,314, filed on Sep. 21, 2007, titled FIXATION DELIVERY DEVICE AND METHOD; and U.S. Provisional Patent Application having Ser. No. 61/012,260, filed on Dec. 7, 2007, titled PELVIC FLOOR TREATMENTS AND ASSOCIATED IMPLANTS, wherein the entireties of said patent applications are incorporated herein by reference.

FIELD OF THE INVENTION

The invention relates to apparatus and methods for implanting a surgical implant, e.g., a pelvic implant for treating pelvic conditions. The methods include an implant to support tissue. Examples of conditions include conditions of the female or male anatomy, and specifically include treatments of pelvic conditions such as female or male urinary and fecal incontinence, and treatment of female vaginal prolapse conditions including enterocele, rectocele, cystocele, vault prolapse, conditions of the pelvic floor, and any of these conditions in combination.

BACKGROUND

Biological implants for supporting tissue, to treat medical conditions, are generally known and used to treat various ailments. Various conditions of female and male pelvic anatomy can be treated by supportive implants. For example, pelvic prolapse conditions, including vaginal prolapse, can be caused by the weakening or breakdown of various parts of the pelvic support system such as the pelvic floor or tissue surrounding the vagina. Similarly, weakened tissues can result in fecal incontinence, urinary incontinence, and levator avulsion and other conditions of the pelvic floor. Broadly, due to the lack of support, structures such as the uterus, rectum, bladder, urethra, small intestine, levator and muscle of the pelvic floor, and vagina, may begin to fall out of their normal positions. Pelvic conditions such as these, as well as other conditions of biologic tissue, can be treated by placement of synthetic or biological implants to support weakened or affected tissues.

SUMMARY

The invention involves implants, systems, kits, and method, for placing a surgical implant for supporting tissue. Embodiments of the invention involve the use of a tool (sometimes referred to as an "insertion tool" or "introducer tool") that includes a shaft and a sheath that engages the shaft in a "covered" and an "uncovered" configuration, relative to the distal shaft end. In one exemplary embodiment a sheath includes a hollow member such as a tube made of hard or flexible plastic, having a shape that can at least partially surround a portion of or a total length of a shaft of an introducer tool. In a covered configuration, the sheath covers and can protect the distal end of the shaft, as well as a tissue fastener that can be engaged with the distal shaft end; in an uncovered configuration the sheath, still engaged with the shaft, does not cover the distal end or an engaged tissue fastener but allows the tissue fastener to contact and become fixed to tissue. In this example embodiment, the sheath (e.g., tube or tubing) can exhibit a profile that allows the introduction and placement of a fixation element (e.g., tissue fastener, or tissue engager such as a self-fixating tip, etc.) into the limited space available during a surgical procedure. The tubing prevents the fixation element and device from catching on pelvic tissue. Additionally, the tubing protects the physician's glove from catching and tearing. The tubing also helps to keep the fixation element in place on the insertion tool.

Both ends of a sheath (e.g., tubing) can be open. The first end can be open to allow entry of the shaft (distal end) of the insertion tool (e.g., fixation device).

Optionally a sheath in the form of a tube or tubing can includes a depth-limiting feature, which refers to a feature that can limit the depth into which a tissue fastener such as a self-fixating tip can penetrate tissue. Upon the act of fixation, attaching a tissue fastener to tissue, the depth-limiting feature can act to prevent inadvertent over-insertion of the fixation element in the fixation site. The second end of the tube is open to allow exposure of the distal end of the tool shaft (e.g., tip) for placement of at tissue fastener. A distal end of a shaft (e.g., tip) may be of a configuration to engage a tissue fastener, e.g., rounded, slotted, domed, blunted, or the like to prevent injury or puncturing of nearby organs.

The insertion tools allow fixation of a tissue fastener when the distal end of a tool shaft (e.g., needle tip), which is engaged with a tissue fastener, is exposed from the sheath (e.g., tubing). This exposure is possible by interaction between the tubing and needle. The interaction may be mechanical (e.g., involving a mechanism built into the handle, shaft, or sheath) or manual (e.g., movement of the sheath by the user). Either of the shaft or sheath may be static while the other moves or, in an alternative embodiment, both components may move. A pin, button, spring, or trigger may be used to initiate the exposure of the needle tip and fixation element.

The present disclosure identifies pelvic implants, components of implants, related devices, systems and kits containing these, and methods of using these for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), conditions of the pelvic floor and result from weakness or trauma of pelvic floor muscles such as the levator ("levator ani") or coccygeus muscle (collectively the pelvic floor), and other conditions caused by muscle and ligament weakness. Exemplary methods can involve treatment of vaginal prolapse, including anterior prolapse, posterior prolapse, or vault prolapse. A method can be transvaginal, involving a single incision in the vaginal tissue, with no external incision.

Any implants or methods described can involve a tissue fastener that is designed to secure an extension portion of an implant to tissue. These may be in the form of a soft tissue anchor, a self-fixating tip, fixation element, etc., which can be inserted into soft tissue or connected to soft tissue, and remain in or contacted with the tissue to support the implant.

An implant can be one that is useful in supporting tissue, e.g., pelvic tissue such as the urethra, rectum, pelvic muscle (e.g., levator ani), rectum, etc. An implant can include features including a support portion for supporting tissue, an extension portion to connect tissue internally to tissue, and optional features such as: an adjusting engagement (one-way or two-way); combinations of a one-way and a two-way adjusting engagement present on a single implant segment (e.g., extension portion piece or segment or scaffold portion piece or segment); scaffold portions as described; multiple pieces (see PCT/US08/009066, filed Jul. 25, 2008, titled PELVIC FLOOR TREATMENTS AND RELATED TOOLS AND IMPLANTS, the entirety of which is incorporated herein by reference). Exemplary embodiments of implants and methods can involve the use of an extension portion piece that includes a mesh portion and a non-mesh portion. Optionally, an implant and method of implanting an implant may further involve a grommet management tool, an adjusting tool, or both.

One embodiment of the invention includes a system that repairs prolapse without external needle passes. The system includes an implant that can be implanted through a single, transvaginal incision. The implant can treat posterior or anterior prolapse by affixing elements of the implant at the sacrospinous ligament, coccygeus muscle, or both. The implant can be placed, secured, and adjusted transvaginally via a single vaginal incision. Unlike certain current systems for use in treating posterior prolapse, this system can be implanted in the body without external trans-gluteal needle passes and is, thus, less invasive. The system generally comprises fixation arms, a center graft, a delivery device, and/or a locking system.

In addition to prolapse, the invention may be used in pelvic treatments such as fecal incontinence, male and female urinary incontinence, and post-prostatectomy repairs. Moreover, the invention may be used in other surgical treatments where tissue anchoring is involved, such as grafts, hernia repair, and shoulder repair.

In one aspect the invention relates to a surgical insertion tool useful for implanting a pelvic implant. The tool includes a handle; a shaft having a proximal shaft end attached to the handle, and a distal shaft end; and a sheath that engages the shaft and allows at least two configurations: a covered configuration in which the sheath covers the distal shaft end, and an uncovered configuration in which the sheath covers a portion of the shaft and does not cover the distal shaft end.

In another aspect the invention relates to a tool comprising a sheath, as described, in combination with an extension portion of an implant. The extension portion includes a tissue fastener at a distal end, and the tissue fastener is capable of engaging a distal end of the shaft.

In another aspect the invention relates to method of implanting an implant in a patient. The method includes: providing a combination of tool that works with a sheath, as described, and an implant, the implant including an extension portion having a tissue fastener at a distal shaft end; engaging the tissue fastener with the distal shaft end, placing the sheath over the shaft and engaged tissue fastener with the sheath in a covered configuration that covers the distal shaft end and engaged tissue fastener, inserting the shaft and engaged tissue fastener into a patient, with the sheath placed over the shaft in the covered configuration, moving the sheath to an uncovered configuration that uncovers the tissue fastener, and fastening the tissue fastener to tissue.

The following patent documents are incorporated herein by reference in their entireties: US Patent Publication No. US 2005/0250977 A1; US Patent Publication No. US 2005/0245787 A1; US Patent Publication No. US 2002/0161382 A1; US Patent Publication No. US 2006/0260618 A1; U.S. Pat. No. 6,652,450; U.S. Pat. No. 6,612,977; U.S. Pat. No. 6,802,807; U.S. Pat. No. 7,048,682; U.S. Pat. No. 6,641,525; U.S. Pat. No. 6,911,003; U.S. Pat. No. 7,070,556; U.S. Pat. No. 6,354,991; U.S. Pat. No. 6,896,651; U.S. Pat. No. 6,652,449; U.S. Pat. No. 6,862,480; U.S. Pat. No. 6,712,772; U.S. Pat. No. 6,981,983; U.S. Pat. No. 7,131,944; U.S. Pat. No. 7,131,943; U.S. Pat. No. 7,267,645; U.S. Pat. No. 6,971,986; U.S. Pat. No. 6,626,916; U.S. Pat. No. 7,407,480; U.S. Pat. No. 7,351,197; and WO 2007/149348 A2, filed Jun. 15, 2007, titled "Surgical Implants, Tools and Methods for Treating Pelvic Conditions."

BRIEF DESCRIPTION OF THE DRAWINGS

FIGS. 1A and 1B illustrate a side, cut-away view of an example of an insertion tool as described.

FIG. 1D illustrates a side view of an example of an insertion tool as described.

FIG. 1E illustrates a closer side view of a distal end of the insertion tool of FIG. 1D.

FIG. 1F illustrates an end view of a distal end of the insertion tool of FIG. 1D.

All drawings are schematic and not to scale.

DESCRIPTION

This description is meant to be illustrative only and not limiting. Other embodiments of this invention will be apparent to those of ordinary skill in the art in view of this description.

The invention involves surgical tools, instruments, assemblies, implantable articles for supporting tissue, and kits and systems that include combinations of these. Examples include tools, instruments, assemblies, and articles for treating pelvic floor disorders such as fecal or urinary incontinence, including stress urinary incontinence (SUI), vaginal prolapse (e.g., anterior or posterior), conditions of the pelvic floor relating to, e.g., muscle of the levator, etc. According to various embodiments a surgical implant can be used to treat a pelvic condition by surgically placing a pelvic implant to treat a condition such as prolapse (e.g., vaginal or otherwise), incontinence (male or female), etc. As more specific examples, an implant can be implanted in a male or a female patient to treat a condition such as urge incontinence; stress urinary incontinence; mixed incontinence; overflow incontinence; functional incontinence; fecal incontinence; prolapse (e.g. vaginal or uterine); enterocele (e.g. of the uterus); rectocele; cystocele; anatomic hypermobility; conditions of the pelvic floor caused by weakness or trauma of pelvic floor muscles such as the levator ("levator ani") or coccygeus muscle (collectively the pelvic floor); other conditions caused by muscle and ligament weakness; and combinations of these.

In general, methods and devices described herein involve an insertion tool that includes a handle, a shaft, and a sheath that can cover at least a portion of the sheath. An exemplary insertion tool can include a handle and a shaft that includes a proximal shaft end attached to the handle, and a distal shaft end. A sheath is a separate piece that can engage the shaft in at least two configurations: a covered configuration and an uncovered configuration. In the covered configuration, a sheath covers the distal shaft end, e.g., in a manner that protects and shields the distal shaft end and an optional tissue fastener that may be engaged with the distal shaft end. In the uncovered configuration the sheath does not cover the distal shaft end and allows the distal shaft end and a tissue fastener that may be engaged with the distal shaft end to engage tissue. In the uncovered configuration the sheath can also cover (completely or partially) the proximal shaft end and a length of shaft between the proximal shaft end and the distal shaft end.

Figure 1C:
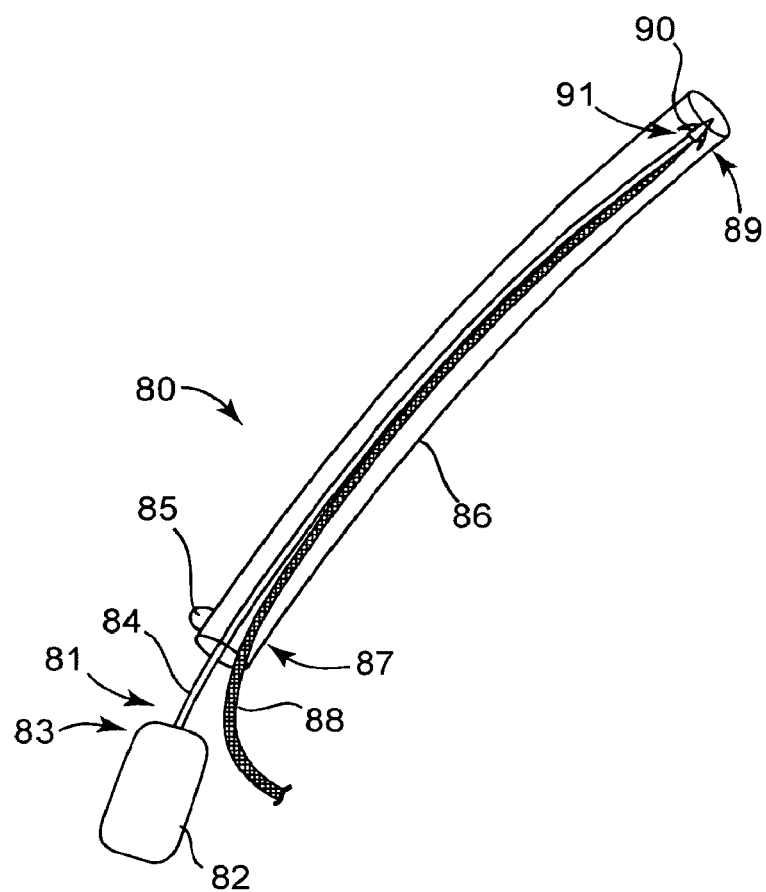
FIG. 1C illustrates a side view of an example of an insertion tool as described.

One example of an insertion tool according to the present description is shown (in a cut-away side-view) at FIGS. 1A and 1B. Tool 10 includes handle 2, shaft 4, and sheath 6. Shaft 4 is a solid needle shaft that includes proximal shaft end 8 attached to distal handle end 12, and distal shaft end 14, designed to engage a tissue fasteners. Recess 16 is a space located at distal end 12 of handle 2, extending longitudinally into handle 2. Generally, the recess is an open space between shaft 4 and a portion of distal handle end 12, that can receive a proximal end of shaft 6 or a portion thereof. As illustrated, recess 16 is the annular space between the outer cylindrical surface of shaft 4 and the inner cylindrical surface 16a of distal end 12 of handle 2. Recess 16 is sized to allow a proximal end (e.g., illustrated as a hollow cylinder) of sheath 6 to fit and become located within recess 16, at different depths, for both covered and uncovered configurations.

The size of a recess (e.g., recess 16) can include a length (along the longitudinal distance of the handle, designated "L") and a width or diameter (along the width of the handle). Another relevant length is length d, which is the distance from a stopping mechanism (pin 22) to the end of recess 16, which is surface 15; this distance, d (see FIG. 1A), is the same as the length of shaft distal end that is uncovered in an "uncovered" configuration (see FIG. 1B). This distance also relates to a maximum depth that the shaft distal end can penetrate into tissue, because the distal end of the sheath will prevent further penetration.

A diameter of a recess, e.g., recess 15, can be sufficient to allow entry of a proximal end of a sheath, and can be slightly larger than the diameter of the sheath. A useful diameter may be, e.g., from 0.5 to 1.0 centimeter. A length (L) of a recess in a handle into which a sheath can enter may be sufficient to allow the sheath to change from a covered to an uncovered configuration by entry or by further entry into the handle, i.e., movement of the sheath along the shaft in the direction toward the handle. The length ca be, e.g., from 1.5 to 3.5 centimeters, such as from 2.0 to 3.0 centimeters.

Still referring to FIGS. 1A and 1B, lever 20 is biased by spring 24 to place pin 22 at a location within recess 16 to contact a surface at a proximal end of sheath 6, to thereby limit movement of sheath 6 into recess 16, toward handle 2. FIG. 1A shows sheath 6 in a covered configuration. In this covered configuration, a distal end of sheath 6 extends to cover and enclose distal shaft end 14. FIG. 1B shows sheath 6 in an uncovered configuration. In this uncovered configuration the distal end of sheath 6 does not enclose distal shaft end 14 but leaves distal shaft end 14 uncovered. The uncovered configuration is achieved, starting from the covered configuration, by moving sheath 6 in a proximal direction (shown by arrow A) to slide sheath 6 toward handle 2, and allowing the proximal end of sheath 6 to become located deeper within recess 16.

Figure 2A:
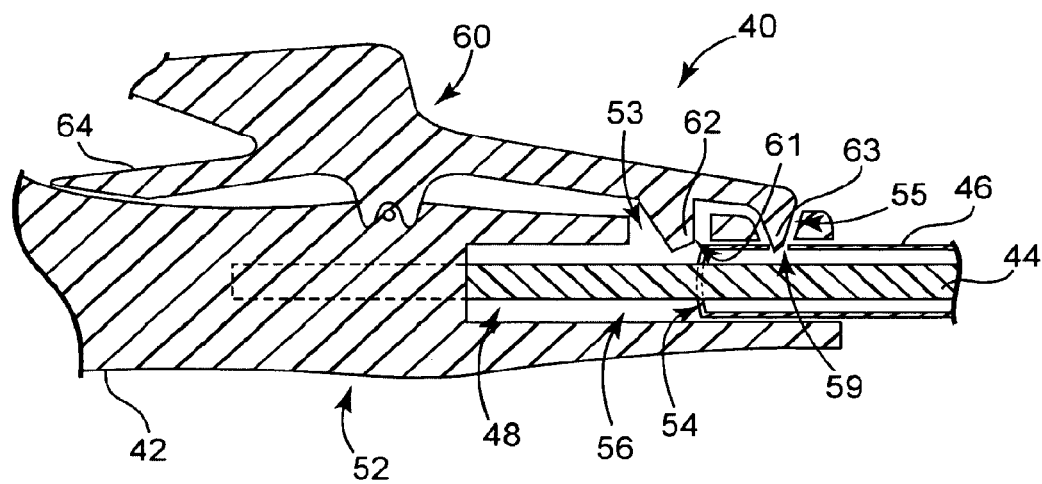
FIGS. 2A and 2B illustrate side cut-away views of an example of a handle of an insertion tool, including a stop mechanism.
Figure 2B:
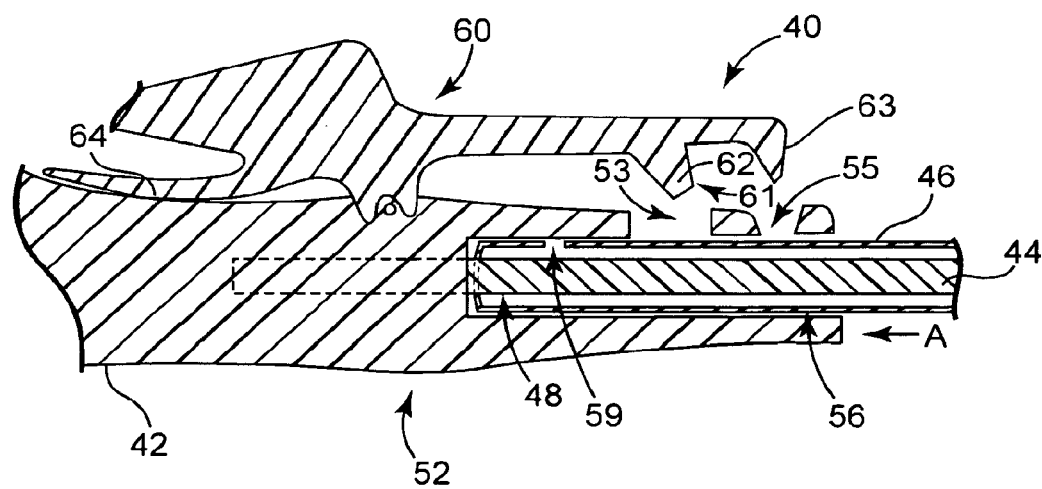

With regard to one embodiment of an insertion tool, FIGS. 2A and 2B include details of structure of a distal handle end including a recess, a proximal shaft end, a sheath, and a mechanical stop that engages the sheath. As shown in a cut-away side view, tool 40 includes handle 42, shaft 44, and sheath 46 (e.g., in the form of a plastic tube). Shaft 44 is a solid needle shaft that includes proximal shaft end 48 attached to distal handle end 52. Recess 56 is a space located at distal end 52 of handle 42, extending longitudinally into handle 42 and sized to allow a proximal end of sheath 46 to fit and become located within recess 56. Lever 60 is biased by spring 64 to place pins (proximal pin 62 and distal pin 63) (e.g., "extensions") at a location within recess 56 and in engagement with sheath 46 to limit movement of sheath 46 into or out of recess 56. A distal surface 61 of proximal pin 62 contacts a proximal end surface 54 of sheath 46, while distal pin 63 engages aperture 59 located at the proximal end of sheath 46. Proximal pin 62 extends through aperture 53 of distal end 52 of handle 42, and distal pin 62 extends through aperture 55 of distal end 52 of handle 42.

FIG. 2A shows sheath 46 in a covered configuration. In this covered configuration, a distal end of sheath 46 (not shown) extends to cover a distal shaft end (not shown) of shaft 44. Also in this covered configuration, sheath 46 extends only partway into recess 56; pins 62 and 63 engage surface 54 and aperture 59 of the proximal end of shaft 46 to prevent movement of sheath 46 in a distal or a proximal direction relative to shaft 44. FIG. 2B shows sheath 46 in an uncovered configuration in which the distal end (not shown) of sheath 46 does not enclose the distal shaft end of shaft 44 (not shown) but leaves the distal shaft end uncovered. The uncovered configuration is achieved, starting from the covered configuration, by moving sheath 46 in a proximal direction (shown by arrow A), to slide sheath 46 toward handle 42 and allow the proximal end of sheath 46 to become located deeper within recess 56 as illustrated at FIG. 2B.

The insertion tool of FIGS. 1A, 1B, 2A, and 2B, involve a stopping mechanism located on a handle that associates with the sheath. In alternate embodiments a stopping mechanism may be located somewhere other than the handle, e.g., along the shaft an insertion tool, or as another alternative a tool may not include or require a stopping mechanism. An example of an insertion tool that does not require a stopping mechanism at a handle is shown at FIG. 1C. Insertion tool 80 includes handle 82, shaft 84, and sheath 86 having proximal end 87 and distal end 89. Shaft 84 is a solid needle shaft that includes proximal shaft end 81 attached to distal handle end 83, and distal shaft end 91, shown in engagement with tissue fastener 90, which is located at a distal end of mesh extension portion 88. (Extension portion 88 may be integrally or otherwise connected to an implant, e.g., a support portion of an implant, or may be a separate piece of an implant.) Thumb surface 85 is located at proximal end 87 of sheath 86 and allows a user to manipulate sheath 86 using a thumb, while holding handle 82, e.g., move sheath 86 from a covered to an uncovered configuration. An optional stopping mechanism (not shown) may be located at the shaft, if desired. The stopping mechanism may include a surface located on shaft 84, such as an extension, that engages a surface on sheath 86; when engagement of the surfaces prevents movement of sheath 86 relative to shaft 84, and disengagement of the surfaces allows movement of sheath 86 relative to shaft 84.

Another alternate embodiment of an insertion tool is one having a stopping mechanism located on a handle, but that does not include a "recess" in the handle that completely surrounds the shaft at the location of the shaft connecting to the handle, e.g., as shown at FIGS. 1A and 1B. Referring to FIG. 1D, insertion tool 92 includes handle 97, shaft 96, and sheath 95 having proximal end 93 and distal end 105. Shaft 96 is a solid needle shaft that includes a proximal shaft end attached to a distal handle end, and a distal shaft end, shown in engagement with tissue fastener 107, which is located at a distal end of mesh extension portion 111. (Extension portion 111 may be integrally or otherwise connected to an implant, e.g., a support portion of an implant, or may be a separate piece of an implant.) A component of a mechanical stop is stop 98, extending distally from handle 97, which can engage a surface at the proximal end of sheath 95. For example to remove the stop, proximal end 93 of sheath 95 can be deflected toward shaft 95 to avoid contact with stop 98 (e.g., by pressure using a user's thumb); the proximal end of sheath 95 can then move into space 99 between shaft 95 and stop 98 to allow sheath 95 to move in direction A and convert sheath 95 from a covered configuration (as illustrated) to an uncovered configuration. Another optional mechanical stop, surface (e.g., bump) 101 located at shaft 95, cooperates with a surface (e.g., depression) 103 in sheath 95. This stop too can be removed by deflecting proximal sheath end 93 in a direction that disengages surface 101 from depression 103, allowing sheath 95 to move in direction A.

A sheath can be made of a rigid, semi-rigid, or non-rigid material that is flexible or inflexible. Examples of general types of materials are those often used with surgical tools, such as metals, ceramics, and plastics or other polymeric materials. For an insertion tool that includes a curved shaft, a sheath can be sufficiently flexible and optionally elastic to allow the sheath to be placed along a desired length of the shaft, including the curve.

Certain preferred materials can be polymeric materials that can be formed into a sheath (e.g., a cylindrical tube having two open ends) to produce a flexible yet self-supporting sheath. A preferred sheath can be flexible in that the sheath can bend to a degree, such as to allow placement onto a curved shaft, and then remain bent if necessary to conform to a curvature of a tool shaft. A preferred sheath can be self-supporting, meaning that if one end of the sheath is supported, the sheath does not substantially fold or bend under the force of the sheath's its own weight.

Polymeric materials that can be useful to produce a sheath, optionally but not necessarily a flexible yet self-supporting sheath, can be polymers that include polyolefins such as polyethylene (e.g., low density polyethylene), polypropylene, polyacrylates, polymethacrylates, polyesters, urethanes, silicones, and the like.

A sheath can exhibit shape and dimension to allow the sheath to cover a shaft of an insertion tool. Certain embodiments of sheaths can include a continuous tube of a length that is approximately the length of the shaft between a distal shaft end and a proximal shaft end at an attachment to a handle, not including a length of the shaft that is contained in a recess of the handle. Exemplary lengths of a sheath will depend on the use of the insertion tool. For an insertion tool intended to be used to place a tissue fastener at a posterior location of a pelvic region, through a vaginal incision, a length of a sheath can be, e.g., from about 15 to 28 centimeters, e.g., from about 18 to 24 centimeters. For an insertion tool intended to be used to place a tissue fastener at an obturator foramen, through a vaginal incision, a length of a sheath can be, e.g., from about 8 to 15 centimeters, e.g., from about 9 to 13 centimeters. If the sheath includes a curve the length includes the full length including the length of curved portion (arclength) in a straightened condition.

The diameter of a sheath such as a semi-rigid tube can be sufficient to allow the hollow interior of the tube to cover a combination of a shaft of an insertion tool and extension portion of an implant, e.g., an inner diameter of a sheath may be from 0.5 to 1.2 centimeters, such as from 0.5 to 0.8 centimeters. According to certain embodiments of sheaths, a diameter at a distal sheath end may gradually reduce, moving distally (see FIG. 1E).

The thickness of a sidewall of a sheath can be consistent along the length of the sheath, and in certain preferred embodiments can be sufficient to result in a sheath that is self-supporting. A sidewall thickness that will be useful to achieve these functions can depend on the sidewall material. A useful sidewall thickness for a sheath made of a polymeric material such as a polyolefin may be in the range from 0.3 to 1.5 millimeter.

A proximal end of a sheath can optionally include an aperture in a sidewall that can be used to engage a mechanical stop such as a pin or an extension, to inhibit movement of the sheath along the length of the insertion tool shaft.

Figure 3A:
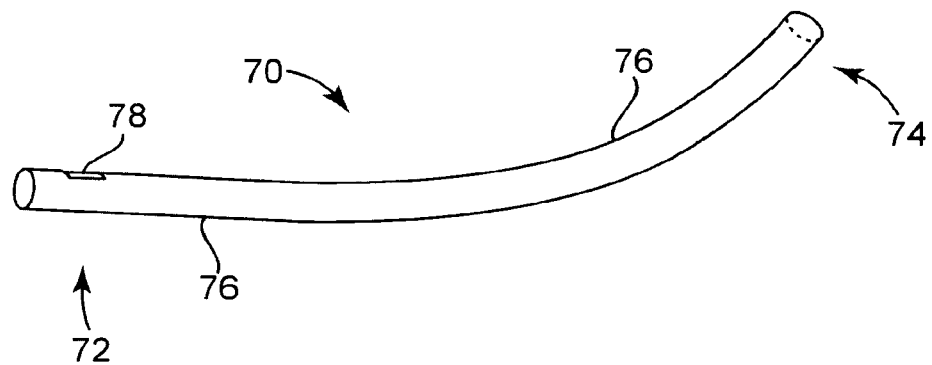
FIGS. 3A and 3B illustrate a side view and a top view, respectively, of an example of a sheath as described.
Figure 3B:
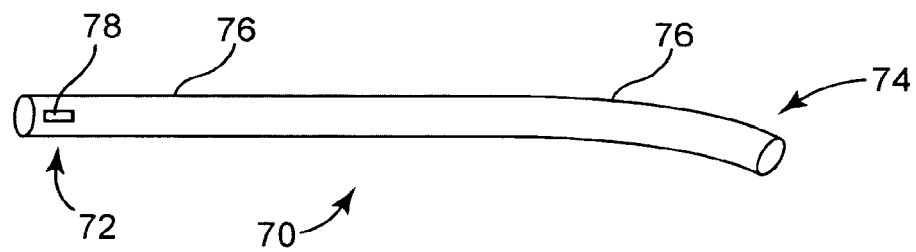

FIG. 3A shows a side view of sheath 70 having proximal end 72, distal end 74, sidewall 76, and aperture 78. As illustrated, sheath 70 is a continuous self-supporting tube made, e.g., of a polymeric material such as polyethylene. The tube is constructed of a solid polymer having openings (end apertures) at each of the proximal and distal ends, and sidewall aperture 78 within the sidewall at proximal end 72. The length of sheath 70 measured from the opposing ends and including the length of the arc of the curve is sufficient to cover a needle of a tool that can reach a posterior pelvic location through a vaginal incision, e.g., from 20 to 22 centimeters. For reaching a different location, e.g., an obturator, through a vaginal incision, the length can be different, e.g., shorter. The inside diameter of the sheath is sufficient to enclose a solid needle shaft and a mesh material of an elongate extension portion, e.g., from 0.5 to 1.0 centimeters. Sidewall aperture 78 is dimensioned to accept a pin, extension, or other mechanical stop useful to limit movement of the sheath relative to an insertion tool shaft, when the pin, extension, or mechanical stop engages sidewall aperture 78.

A sheath can include a distal end that covers a tissue fastener, and also optionally exhibits a reduced profile for easing insertion of the sheath distal end through tissue. For example a sheath distal end can be tapered to reduce a cross-sectional dimension such as diameter. FIGS. 1D, 1E, and 1F illustrate a tapered sheath distal end. Referring to FIGS. 1E (side cross section) and 1F (end view), sheath distal end 105 includes a tapered profile embodied as a diameter that decreases along the length of the sheath distal end, moving distally. The tapered distal end can preferably include an opening that allows a tissue fastener to pass through the reduced-diameter distal end, such as by allowing passage of lateral extensions of a self-fixating tip. FIG. 1F shows lateral slots 117 that allow lateral extensions 118 to pass through distal end 115.

In use, a tool as described (e.g., tool 10, tool 40, tool 80, tool 92, or as otherwise described) can be used to place an implant in a patient. General steps of using a tool as described can include engaging a tissue fastener of an implant with a distal shaft end (e.g., 14) and placing a sheath (e.g., 6, 46) over the shaft and engaged tissue fastener. Generally, in the covered configuration, extension portion of the implant (e.g., an extension portion piece), or a segment thereof, and the shaft of the insertion tool, will be covered at least in part by the sheath, i.e., will be located within the sheath. See, e.g., FIGS. 1C and 1D. The assembly of the tool with sheath and engaged tissue fastener can be inserted into a patient in the covered configuration with the distal sheath end covering the distal shaft end and engaged tissue fastener. Once inside, the position of the sheath can be changed from the covered to an uncovered configuration to expose the tissue fastener at the distal shaft end. In an uncovered configuration, as an example, a length of from 0.3 to 1.5 centimeters of the distal end of the shaft can be uncovered, such as from 0.8 to 1.5 centimeters (this measurement can be done either with an engaged tissue fastener, in which the length of the tissue fastener is included, or without an engaged tissue fastener). This change in configurations can optionally be performed in conjunction with a movement of a mechanical stop, e.g., at the handle, along the shaft, or at any selected location of the tool. The exposed tissue fastener can be fastened to (e.g., fixated to, inserted into, or otherwise engaged to) tissue, and the tool including the sheath can be removed.

Exemplary implants that can be used for placement by an insertion tool as described can be useful for supporting any tissue of a living body, including but not limited to pelvic tissue. When used to support pelvic tissue an implant can include a tissue support portion that can be used to support pelvic tissue such as a urethra (which includes the bladder neck), bladder, rectum, vaginal tissue (Level 1, Level 2, Level 3, or combinations of these), pelvic floor tissue (e.g., levator muscle tissue), etc. During use, the tissue support portion is typically placed in contact with and attached to tissue to be supported, such as by attachment using one or more sutures. An implant can additionally include one or more extension portion attached or attachable to the tissue support portion. An extension portion may be a portion referred to as a "scaffold" portion, which can be attached to a tissue support portion or another extension portion. A tissue fastener, dilator, or connector, etc., can be included at an end of an extension portion.

The tissue support portion can be designed to support a specific type of pelvic tissue such as the urethra, bladder (including the bladder neck), vaginal tissue (anterior, posterior, apical, etc.), rectum, tissue of the pelvic floor such as levator muscle, etc. The tissue support portion can be sized and shaped to contact the desired tissue when installed, e.g., as a "sling" or "hammock," to contact and support pelvic tissue.

Extension portions are pieces of material, generally elongate or otherwise extended from a tissue support portion, or in the case of a scaffold portion from another extension portion. Embodiments of extension portions can be useful to either pass through or attach to tissue of the pelvic region to thereby provide support for the tissue support portion and the supported tissue. One or multiple (e.g., one, two, four, or six) extension portions can extend from a tissue support portion for attachment to tissue in the pelvic region, such as by extending to an internal anchoring point (or "fixation point") (for attachment by bone anchor, tissue fastener, etc. as described), or through a tissue path to an external incision.

An implant can optionally include a scaffold portion (which can be considered a type of extension portion) that can be extended internally within a patient and secured to tissue of a pelvic region or to a location of the implant. A scaffold portion can be used to support a tissue support portion or another extension portion attached to the scaffold portion, e.g., along a length of the scaffold portion and between two ends of the scaffold portion. A scaffold portion can have two ends. Either end can be attached internally to tissue of the pelvic region, or to the implant, such as to a tissue support portion, another extension portion, or another scaffold portion. An end of a scaffold portion can be securely (nonadjustably) attached to a tissue support portion or another extension portion, such as by a suture, rivet, staple, etc.; may be integrally formed with the tissue support portion or extension portion; or may be adjustably attached to a tissue support portion or an extension portion using an adjusting engagement. A scaffold portion may also optionally include an adjusting engagement along the length of the scaffold portion.

A "multi-piece" implant refers to an implant that includes one or more "support portion piece," and one or multiple "extension portion piece" (which may be a "scaffold portion piece") as separate pieces of the implant. An extension portion piece or scaffold portion piece can be separate from a support portion piece, and can be connected through one or multiple adjusting engagements. The support portion piece includes a tissue support portion.

Exemplary implants can be made of materials and may be generally shaped and sized with certain individual features that may be found in previous implants, but can be modified to include features as described herein such as a scaffold portion, an adjusting engagement, any of the various tissue fasteners described herein, multi-piece construction, etc., and can be adapted for use according to methods described herein, e.g., involving tools that incorporate a sheath. An implant can have features described in the following exemplary documents: U.S. patent application Ser. No. 10/834,943, filed Apr. 30, 2004; U.S. patent application Ser. No. 10/306,179, filed Nov. 27, 2002; U.S. patent application Ser. No. 11/347,063, filed Feb. 3, 2006; U.S. patent application Ser. No. 11/347,596, filed Feb. 3, 2006; U.S. patent application Ser. No. 11/347,553, filed Feb. 3, 2006; U.S. patent application Ser. No. 11/347,047, filed Feb. 3, 2006; U.S. patent application Ser. No. 11/346,750, filed Feb. 3, 2006; U.S. patent application Ser. No. 11/398,368, filed Apr. 5, 2005; U.S. patent application Ser. No. 11/243,802, filed Oct. 5, 2005; U.S. patent application Ser. No. 10/840,646, filed May 7, 2004; and International patent application number PCT/US2006/028828, having an International Filing Date of Jul. 25, 2006; International Application No. PCT/US2007/004015 entitled "SURGICAL ARTICLES AND METHODS FOR TREATING PELVIC CONDITIONS," filed Feb. 16, 2007; International Publication No. WO 2008/013867 entitled "SURGICAL ARTICLES AND METHODS FOR TREATING PELVIC CONDITIONS," published Jan. 31, 2008; International Application No. PCT/US2008/08006 entitled "SURGICAL ARTICLES AND METHODS FOR TREATING PELVIC CONDITIONS," filed Jun. 27, 2008; International Application No. PCT/US2008/09066 entitled "PELVIC FLOOR TREATMENTS AND RELATED TOOLS AND IMPLANTS," filed Jul. 25, 2008; and International Application No. PCT/US2008/000033 entitled "METHODS FOR INSTALLING SLING TO TREAT FECAL INCONTINENCE, AND RELATED DEVICES," filed Jan. 3, 2008; the entireties of each of these disclosures being incorporated herein by reference in their entireties.

Examples of commercial implants include those sold by American Medical Systems, Inc., of Minnetonka Minn., under the trade names Apogee®, Perigee®, and Elevate™ for use in treating pelvic prolapse (including vaginal vault prolapse, cystocele, enterocele, etc.), and Sparc®, Bioarc®, Monarc®, and MiniArc™ for treating urinary incontinence. Implants useful according to the present description can include one or more features of these commercial implants.

An implant may include portions, pieces, or segments, that are synthetic or of biological material (e.g., porcine, cadaveric, etc.). Extension portions and scaffold portions (made of a single piece or of more than one piece) may be, e.g., a synthetic mesh such as a polypropylene mesh. A tissue support portion may be synthetic (e.g., a polypropylene mesh) or biologic. (As used herein, the term "portion of implant" (or "implant portion") refers generally to any piece, segment, or portion (e.g., extension portion or scaffold portion) of an implant. The term "segment of implant" (or "implant segment") refers to an elongate length of implant material, such as a length of an elongate section of an extension portion or a scaffold portion.)

Examples of implants for treating vaginal prolapse (e.g., anterior vaginal prolapse, posterior vaginal prolapse, vaginal vault prolapse) can include a central support portion and from two to four to six extension portions, and may take the form of an integral piece of mesh or other implant material, or multiple pieces of mesh or other implant material attached in a modular fashion. See, e.g., Assignee's copending U.S. patent application Ser. Nos. 11/398,369; 10/834,943; 11/243,802; 10/840,646; PCT/2006/028828; among others. Particularly useful examples of implants for treating vaginal prolapse, using any one or a combination of devices or methods as described herein can be implants described in Assignee's copending International Patent Application No. PCT/US2007/014120, entitled "SURGICAL IMPLANTS, TOOLS, AND METHODS FOR TREATING PELVIC CONDITIONS," filed Jun. 15, 2007, and International Application No. PCT/US2008/09066 entitled "PELVIC FLOOR TREATMENTS AND RELATED TOOLS AND IMPLANTS," filed Jul. 25, 2008, the entirety of which is incorporated herein by reference.

According to various embodiments of implants described herein, an implant can include pieces or portions that are adjustably connected together by an adjusting engagement, which may be either a one-way adjusting engagement or a two-way adjusting engagement, to allow a portion or a segment of an implant to be moved relative to another portion or segment, and adjusted as to length, tension, or positioning. As an example, an extension portion piece can be attached to a support portion piece at an adjusting engagement to allow adjustment of a length of extension portion. Alternately or in addition, a scaffold portion or scaffold portion piece can be attached to a support portion piece or to an extension portion at an adjusting engagement to allow adjustment of length or tension of a scaffold portion.

Some adjusting engagements can allow free two-way movement of one piece relative to another piece (e.g., a "two-way" adjusting engagement). This type of adjusting engagement allows easy movement of a segment of implant in two directions through an adjusting engagement. The force needed to move the segment of implant in one direction is substantially equal to the force needed to move the segment in the opposite direction, and, preferably, the two-way adjusting engagement does not substantially hinder the movement of a segment of implant through the adjusting engagement with frictional surfaces such as extensions (e.g., "teeth") extending into an aperture through which the segment of implant is moved. As an example, a two-way adjusting engagement may include an open (smooth) aperture that may be circular, oval, elongate such as in the form of a slit or slot, etc. The aperture may optionally be reinforced by a reinforcement of a shape that is similar to the aperture, such as by a fabric or a polymeric material such as a grommet (e.g., a "loose grommet" or "eyelet"), which may be circular, or may be of another shape. The reinforcement (e.g., grommet) defines a reinforced aperture through which a segment of implant can pass relatively freely and with the same resistance two different directions.

Other adjusting engagements may allow for one-way adjustment such as shortening of a length of the extension portion or scaffold portion. These adjusting engagements can be referred to as "one-way" adjusting engagements, and allow adjustment of a length of an implant portion in one direction and not in an opposite direction. An exemplary one-way adjusting engagement can include an aperture through which a segment of implant can extend, and one or multiple surfaces (e.g., extensions or teeth) that frictionally engage the segment of implant, e.g., by extending into or toward the aperture or otherwise contacting the segment of implant to inhibit movement of the segment of implant relative to the adjusting engagement. The one-way engagement can preferentially allow movement of the segment of implant through the aperture in one direction while inhibiting movement of the segment of implant in an opposing direction.

Still other embodiments of adjusting engagements may allow for two-way adjustment of a length of extension portion in one configuration (an "open" configuration), and further include a structure or mechanism that can be switched, activated, moved, removed, closed, or opened, to secure a frictional adjusting engagement at a selected location to prevent movement in either direction.

In use of an adjusting engagement, a tissue fastener at one end of an extension portion piece can placed at tissue as desired (and "fixed" or "secured") and a second (loose) end of the extension portion piece can be passed through an adjusting engagement, e.g., a two-way adjusting engagement. The engagement is adjusted to place the support portion piece at a desired position (length) of the extension portion piece. A second adjusting engagement, e.g., a one-way grommet, is slid onto the loose end of the extension portion piece and slid along the extension portion piece to a location at the two-way adjusting engagement. The one-way adjusting engagement moves easily along the extension portion piece in the direction toward two-way adjusting engagement, and does not move easily in the opposite direction. Once placed in position near the two-way adjusting engagement of the support portion piece, the support portion piece is prevented from moving along the extension portion piece in the direction of the one-way adjusting engagement.

Implants as described can include a tissue fastener (also referred to herein as a "fixation element") at a distal end of an extension portion, which is the end not attached to a tissue support portion or other portion or segment of an implant. (The term "distal" as used herein may be used to refer to an end of a structure that is "away from" a different structure, such as a distal end of an extension portion that is the end away from a connection to a tissue support portion. The term "distal" may also (based on arbitrary selection) generally refer to a location that is relatively more posterior to a patient, and relatively farther away from a surgeon performing a method as described; "proximal" generally refers to a location that is relatively more anterior to a patient, and relatively closer to a surgeon performing a method as described. Any other convention, such as an opposite convention, could alternately be used to refer to features of devices and methods as described.)

A tissue fastener can be of various types, including, as examples, a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical Implants, Tools, and Methods for Treating Pelvic Conditions, filed Jun. 15, 2007, the entirety of which is incorporated herein by reference.) An implant may also have extension portions that do not include a tissue fastener at a distal end, for example if the distal end is designed to be secured to tissue by other methods (e.g., suturing), or is intended to pass through an external incision, in which case the extension portion may include a connector, dilator, or dilating connector, which connects to an elongate tool that can be used to either push or pull the connector, dilator, or dilating connector through a tissue path to an external incision.

A tissue fastener can be placed at and secured (or "fixated" or "fixed") within internal tissue of the pelvic region to support the implant and pelvic tissue that is supported by the implant. A tissue fastener can be placed at muscle tissue of an obturator foramen (e.g., obturator internus muscle), tissue of an arcus tendineus or surrounding an arcus tendineus, tissue of a sacrospinous ligament, tissue in a region of a sacrospinous ligament, tissue of a coccyx region, tissue of a region of an ischial spine, tissue of coccygeous muscle, tissue of iliococcygeous muscle, tissue of a uterosacral ligament, tissue of levator muscle, or at other tissue of the pelvic region.

One embodiment of a tissue fastener is a self-fixating tip. A "self-fixating tip" in general can be a structure (sometimes referred to as a soft tissue anchor) connected to an extension portion that can be implanted into tissue (e.g., muscle tissue, tendon tissue, or ligament tissue) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through an incision to reach the interior of the pelvic region. The self-fixating tip may engage the insertion tool at an internal channel of the self-fixating tip, at an external location such as at a base, or at a lateral extension, as desired.

Exemplary self-fixating tips can include one or more lateral extensions that allow the self-fixating tip to be inserted into soft tissue and to become effectively anchored in the tissue. A lateral extension may be moveable or fixed. The size of the self-fixating tip and optional lateral extensions can be useful to penetrate and become anchored into the tissue. Exemplary self-fixating tips are described in Assignee's copending international patent application PCT US2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion (also meaning, as used herein, a scaffold portion). The base extends from the proximal base end to the distal base end and can optionally include an internal channel extending from the proximal base end at least partially along a length of the base toward the distal base end. The optional internal channel can be designed to interact with (i.e., engage) a distal end of an insertion tool to allow the insertion tool to be used to place the self-fixating tip at a location within pelvic tissue of the patient. Embodiments of self-fixating tips also include one or more lateral extension extending laterally (e.g., radially) from the base, such as from a location between the proximal end and the distal end, from a location at the distal base end, or from a location at the proximal base end.

A self-fixating tip can be made out of any useful material, generally including materials that can be molded or formed to a desired structure and connected to or attached to an end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

Other embodiments of tissue fasteners can be various, and can include types of fixed or moveable structures capable of securing an implant extension portion or an implant scaffold portion to soft tissue. According to methods described herein, the tissue fastener can be designed to removably engage an end of a shaft of an insertion tool, while also being attached to an end of an extension portion, and also capable of being covered by a sheath when engaged at the end of the shaft. Examples of tissue fasteners may include those sometimes referred to as soft tissue anchors and a self-fixating tips, and also include spring-biased fasteners that can be inserted into tissue or that may grasp and hold tissue, fasteners that include a male component that engages a female component (e.g., within tissue), or that involve extensions (tines or teeth) that can be extended from a delivery tool to splay laterally into soft tissue.

Embodiments of implants and kits according to the present description can include extension portion pieces, as described, of various constructions. Generally, an extension portion piece can include a segment (referred to herein as a "mesh portion," but not necessarily of mesh) having a tissue fastener at one end. The extension portion piece can be configured to engage a support portion piece in a manner that allows the mesh portion to provide a structure that includes an extension portion having an adjustable length. An end of the extension portion piece can be placed through an adjusting engagement of a support portion piece, and the end of the support portion piece that includes the tissue fastener forms an extension portion between tissue (with which the tissue fastener becomes engaged) and the support portion piece (to which the extension portion is engaged at the adjustable engagement).

Embodiments of extension portion pieces used with methods and implants described herein may also include a non-mesh portion. A non-mesh portion may be, for example a suture, a set of sutures, a tape, or processed (e.g., melted or compressed) mesh. A non-mesh portion can facilitate placement or movement of an extension portion piece relative to a support portion piece, e.g., through an adjusting engagement. A mesh of an extension portion piece may be unwieldy for placing into an adjusting engagement such as a small-diameter grommet, small-dimension slot, toothed-slot, etc. A non-mesh portion can allow easier placement (threading) of an end of an extension portion piece through an aperture of an adjusting engagement by providing a less wieldy, integral (non-mesh), more easily managed end. A non-mesh tape, for example, may be more easily inserted into a slot or a toothed-slot of a one-way or a two-way adjusting engagement. A cylindrical non-mesh portion such as a flexible yet rigid plastic "rod" may be more easily inserted into a round aperture such as an aperture of a grommet, compared to a loose end of a mesh material.

A non-mesh portion may allow for easier adjustment of the extension portion piece within an adjusting element. A non-mesh can exhibit reduced cross section, and friction compared to a mesh material. Additionally, an extension portion piece made of a full length of mesh material can undesirably engage tissue that can stick to mesh and become lodged in an adjusting element. A non-mesh portion can be less prone to sticking to tissue during use.

Mesh and non-mesh portions of an extension portion piece can be dimensioned to allow the mesh portion to engage an adjusting engagement when adjusted to a desired length and when a distal end tissue fastener is fastened to tissue as desired. A non-mesh portion can be of a length to allow manipulation and adjustment of the extension portion piece. Exemplary lengths of a total extension portion piece can be in the range from 4 to 10 inches, including a mesh portion and a non-mesh portion (if present). For an extension portion piece that includes a mesh portion and a non-mesh portion, a mesh portion can be, for example, from 1 to 4 inches in length and a non-mesh portion (e.g., polymeric rod, suture, etc.) can be, for example, from 3.5 to 5.5 inches in length.

Figure 4:
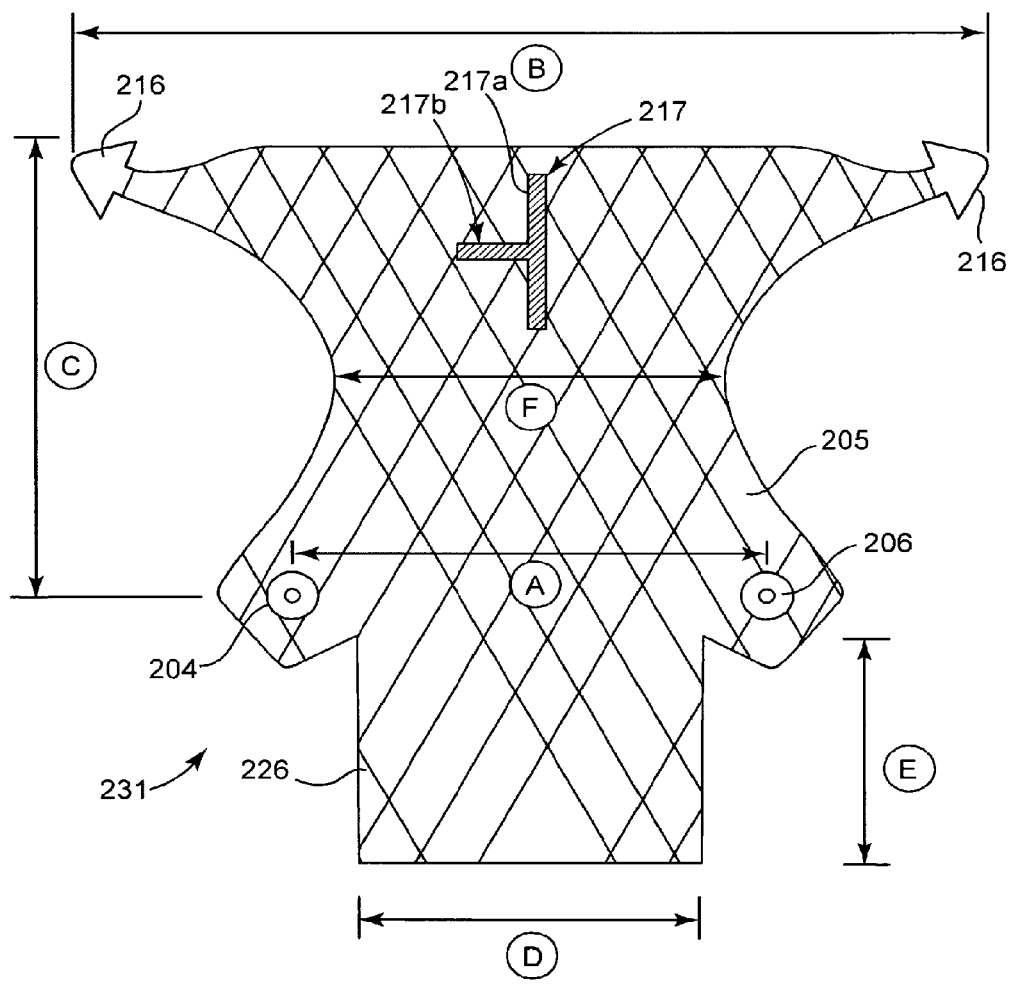
FIG. 4 illustrates an exemplary implant piece as described.

FIG. 4 illustrates one example of a useful implant (231), having certain features described herein. Support portion piece 205 can be placed, e.g., to treat anterior vaginal prolapse. Implant 200 includes support portion piece 205 having two-way apertures (e.g., grommets or openings) 204 and 206. Extension portion pieces (not shown) can be threaded loosely through each of apertures 204 and 206, respectively, to allow substantially free two-way movement of each extension portion piece through each aperture (204, 206), for adjustment. Tissue fasteners 216 can be placed at opposing obturator foramen of a patient, while support portion piece 205 is placed to support vaginal tissue. Posterior tissue support extension 226 is optional and may be place to support posterior vaginal tissue. Adjusting engagements 204 and 206 may be one-way adjusting engagements (e.g., grommets) or two-way adjusting engagements (e.g., grommets). Extension portion pieces (not shown) may include a length that is entirely mesh, or may include a mesh portion and a non-mesh portion, FIGS. 5A and 5B or otherwise described herein. A grommet management tool as illustrated at either of FIGS. 6A and 6B, or as otherwise described herein, can be used to place a grommet on each non-mesh portion of such extension portion pieces. An adjusting tool may be used to adjust position of an adjusting engagement.

Mark 217 on implant 231 includes a centerline mark and an orientation mark. The mark is on one side of the implant, e.g., to identify a top surface of the implant relative to a bottom surface. The centerline mark 217a runs vertical (as illustrated), which is from an anterior to a posterior location on the implant, and is located to mark the centerline of the implant piece. A portion of the mark, 217b, perpendicular to centerline mark 217a, indicates a particular side of the implant, which as illustrated is a patient-left-side of the implant. This may be useful, for example, to confirm correct orientation of the implant such as that the correct side of the implant is being placed upward.

Exemplary dimensions of an implant as shown at FIG. 4 can be: length A, from 5 to 7 centimeters, e.g., from 5.5 to 6.5 centimeters; length B, from 10 to 12 centimeters, e.g., from 10.5 to 11.5 centimeters; length C, from 5.5 to 7.5 centimeters, e.g., from 6 to 7 centimeters; length D, from 3.5 to 5.5 centimeters, e.g., from 4 to 5 centimeters; length E, from 2 to 4 centimeters, e.g., from 2.5 to 3.5 centimeters; and length F, from 4 to 6 centimeters, e.g., from 4.5 to 5.5 centimeters.

Figure 5A:
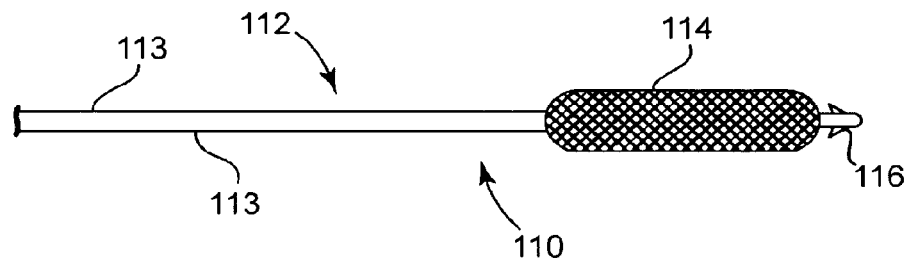
FIGS. 5A and 5B illustrate exemplary extension portion pieces, as described.

FIG. 5A illustrates an example of an extension portion piece (alternately referred to herein as a "fixation arm") that includes a mesh portion and a non-mesh portion. Extension portion piece 110 includes mesh portion 114 and non-mesh portion 112, in the form of two sutures 113. Tissue fastener (e.g., a self-fixating tip) 116 is attached to a distal end of mesh portion 114. Sutures 113 are attached to a proximal end of mesh portion 114, such as by knots. Non-mesh portion 112 is illustrated to be in the form of two sutures, but may alternately by more or fewer sutures, such as one suture, or three sutures, optionally tied or braided. Still alternate forms of non-mesh portion 112 may be a polymeric tape, a narrow fabric, or the like, any of which can be selected to be easily threaded through an aperture of a desired adjusting engagement.

Figure 5B:
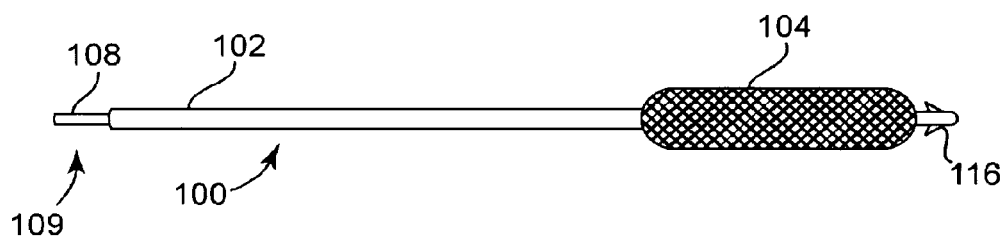

FIG. 5B illustrates another example of an extension portion piece (alternately referred to herein as a "fixation arm") that includes a mesh portion and a non-mesh portion. Extension portion piece 100 includes mesh portion 104 and non-mesh portion 102. Tissue fastener (e.g., self-fixating tip) 106 is attached to a distal end of mesh portion 104. Polymeric (e.g., polypropylene) rod 102 is attached to (preferably integral to) a proximal end of mesh portion 104. Polymeric rod 102 can be formed by any method and may be integrally attached to mesh portion 104, or attached by any technique. As an example, polymeric rod 102 may be prepared by starting with a length of mesh material that is integral to mesh portion 104. The length of mesh can be heat treated at a desired melting temperature (according to the type of polymer of the mesh) to melt the mesh into a polymeric rod having stiff yet flexible mechanical properties. For polypropylene, a desired heat-treating temperature may be in the range from 450 to 520 degrees Fahrenheit. Polymeric rod 102 can be of useful dimensions, such as a length in the range of about 3.5 to 5.5 inches and a width dimension (e.g., diameter) useful to engage a dilator, e.g., about $1/16$ of an inch, or from about 1 to 4 millimeters.

Optionally, and as illustrated at FIG. 5B, proximal end 109 of polymeric rod 102 can be shaped to accept or matingly engage an end of a grommet-management tool, such as a polymeric rod, that can facilitate placement of a grommet or other adjusting engagement onto a proximal end of a non-mesh portion of an extension portion piece. Absent some type of grommet-management tool, a user of an extension portion piece such as extension portion piece 100, may place a grommet (e.g., a one-way grommet) onto a proximal end of a non-mesh portion by hand, using fingers. This can be clumsy, especially in potentially confined or deep locations of a pelvic region. A grommet management tool holds one or multiple grommets. An end of the grommet management tool can engage a proximal end of a non-mesh portion of an extension portion piece in a manner to allow the end of the grommet management tool to align and mate against the proximal end of the extension portion piece. Once the ends are engaged, a grommet can slide from the grommet management tool, directly onto the proximal end of the non-mesh portion of the extension portion piece.

A grommet management tool may contain a single grommet, or multiple grommets, and can be used to transfer the one or multiple grommets onto multiple different extension portion pieces of a single or multiple pelvic implants. Advantageously, a grommet management tool can ensure that control of a grommet (or other adjusting engagement) and a location of a grommet are not lost during a surgical procedure, and a grommet can be prevented from becoming a free-standing, separate piece with the potential of becoming lost during a surgical procedure.

Figure 6A:
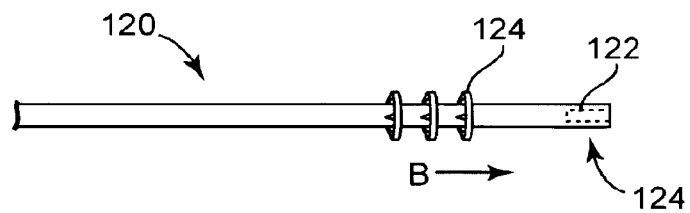
FIGS. 6A and 6B illustrate exemplary grommet-management tools, as described.

FIG. 6A illustrates grommet management tool 120, which is a rod, such as a polymeric (e.g., polypropylene) rod with a diameter that matches a diameter of polymeric rod 102. One-way (alternately two-way) grommets 124 are aligned along a length of grommet management tool 120. Distal end 124 includes channel or bore 122 that is complementary to cylindrical extension 108 at proximal end 109 of extension portion piece 100. These complementary surfaces can be engaged to allow transfer of a grommet from tool 120 to polymeric rod 102.

In use, non-mesh portion 102 of extension portion piece 100 can be passed through an adjusting engagement of an implant. The implant and extension portion piece can be manipulated and placed as desired, such as at locations within a pelvic region. Channel 122 of grommet management tool 120 can be placed over cylindrical extension 108, and a grommet 124 can be slid in direction B (see FIG. 6A) and transferred from grommet management tool 120 onto proximal end 109 of extension portion piece 100. One-way grommets 124 move easily along an extension portion piece in direction B, and are inhibited from moving in a direction opposite of direction B when placed on a mesh portion such as mesh portion 104. Once placed onto extension portion piece 100, grommet 124 can slide to engage mesh portion 104, and contact the adjusting engagement of the tissue support portion or support portion piece to secure a relative position of mesh portion 104 to the tissue support portion or support portion piece, e.g., to fix a length of an extension portion of mesh portion 104.

A grommet management tool such as tool 120 can be made of a plastic, metal, or other useful material. As an example, a grommet management tool can be prepared in the same manner used to make a polymeric rod non-mesh portion 102, such as by melting a length of mesh and molding to form a polymeric rod. Other methods can also be used, such as by extruding, injecting molding, etc.

As illustrated, the engagement between distal end 124 of grommet management tool 120, and proximal end 109 of non-mesh portion 102, includes complementary cylindrical surfaces. Other engagements can also be useful, such as complementary conical surfaces, square surfaces, etc.

Optionally, a feature of a non-mesh portion of an extension portion piece, or of a grommet management tool, may include a feature that allows a one-way grommet to pass only if the one-way grommet is correctly oriented for movement in a desired direction. An example of this feature can be a shoulder or notch located at a proximal end of a non-mesh portion of an extension portion piece (or, alternately, at a distal end of a grommet management tool).

Figure 6B:
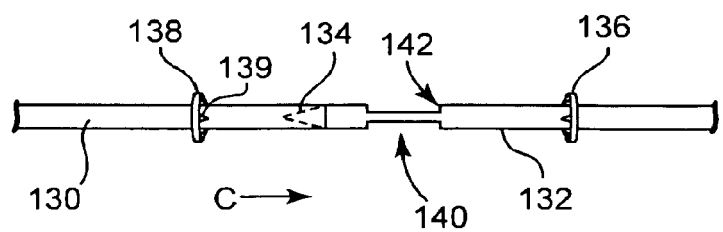

Referring to FIG. 6B, grommet management tool 130 engages proximal end 132 of an extension portion piece. The engagement includes complementary conical surfaces 134 to allow alignment and mating between the two ends. Notch 140 and shoulder 142 allow one-way grommet 136 to transfer from tool 130 onto non-mesh portion 132, because grommet 136 is oriented in a direction to allow movement in direction C and inhibit movement in a direction opposite of direction C. Notch 140 and shoulder 142 prevent one-way grommet 138 from transferring onto non-mesh portion 132. Grommet 138 is oriented in a direction to allow movement in the direction opposite of direction C and not in direction C. Teeth 139 of grommet 138 would engage shoulder 142 and stop grommet 138 from moving past shoulder 142 in direction C. Notch 140 and shoulder 142 are illustrated to be located on non-mesh portion 132, but alternately could be included on grommet management tool 130.

A system as described also includes an insertion tool that generally includes a handle and a shaft. The shaft can be a solid structure such as a solid needle that is optionally curved in two or three dimensions. The distal end of the needle can include a surface that engages a tissue fastener by fitting inside a channel in a base of the tissue fastener, e.g., as with embodiments of self-fixating tips. Alternately, a shaft can include a hollow center such as that of a trocar, or a moveable mechanism that can engage a self-fixating tip by grasping or other mechanical engagements. Various different types of surgical tools, including insertion tools, may generally be useful to engage and place a tissue fastener secured to an extension portion (or, as described herein, a scaffold portion) of an implant as described. Various types of insertion tools are known, and these types of tools and modifications thereof can be used according to the present description to install an implant.

Examples of useful insertion tools include those types of tool that generally include a thin elongate shaft (e.g., needle); a handle attached to one end (a proximal end) of the shaft; and an optional distal end (or "tip") of the shaft adapted to engage a tissue fastener connected to extension portion (including a scaffold portion). The needle can facilitate placement of the distal end of the extension or scaffold portion at a desired anatomical location that may be internal or through a tissue path to an external incision.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; and PCT application number 2006/0260618; each of which is incorporated herein in its entirety by reference. Tools described in these patent documents are designed for placement of an implant in a pelvic region for the treatment of prolapse, male or female incontinence, etc.

Exemplary insertion tools can be similar to or can include features of tools described in the above-referenced patent documents. For use according to certain methods described herein, those insertion tools may be modified, such as to allow the insertion tool to be used to place a self-fixating tip through a vaginal or a medial incision, to engage tissue within the pelvic region. The insertion tool can be designed, shaped, and sized, to include an elongate shaft that may be straight or that may be curved in two or three dimensions, that can be inserted through a vaginal incision (for female anatomy) or through a perineal incision (for male anatomy), and extend from that incision to or through pelvic tissue for placement of a distal end of an extension portion.

Figure 7A:
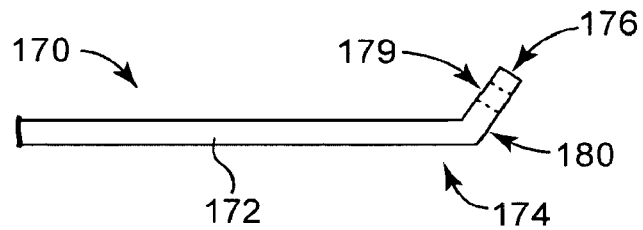
FIGS. 7A, 7B, 8A, and 8B illustrate exemplary adjusting tools, as described.
Figure 7B:
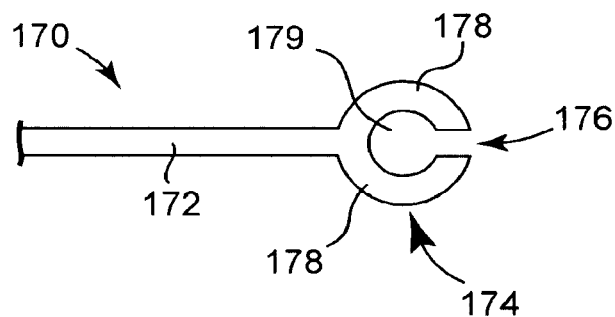

Another tool for optional use in a method as described, such as methods that involve an adjusting mechanism, is an adjusting tool. An adjusting tool can be an elongate tool that includes a distal end that engages an adjusting mechanism, to manipulate and optionally cause movement of the adjusting mechanism relative to a portion of implant. FIGS. 7A and 7B show side and top views of adjusting tool 170, useful for moving an adjusting engagement such as a grommet along a length of a segment of an implant such as a segment of an extension portion or a scaffold portion. Tool 170 includes elongate shaft 172 and distal end 174. Slot 176 at distal end 174 can be slid past a segment of implant to place a segment of implant at a location within aperture 179. Aperture 179 is defined in part by opposing arms 178 (illustrated to be curved, but optionally straight, angled, etc.) that extend laterally and optionally distally from a distal end of shaft 172, to define aperture 179 and slot 176. Bottom surfaces of arms 178 can be used to apply pressure to an adjusting engagement (e.g., grommet) located on the segment of implant, and move the grommet, preferably in a direction along the segment of implant to adjust a length of an extension portion or scaffold portion. Slot 176 is optional, and distal end 174 could alternately include a closed aperture through which a portion of implant could be threaded place distal end 174 in contact with an adjustable engagement.

The dimensions of the slot (optional) and aperture can be useful to engage a segment of implant. A slot, for example, may define an opening that is in the range from 0.5 to 1.2 centimeters, e.g., from 0.5 to 1.0 centimeter. An aperture may have the same or similar dimensions, or may be the same width or wider than the slot, such as having a diameter in the range from 0.5 to 1.2, e.g., 0.5 to 1.0 centimeter. Surfaces for engaging an adjusting engagement may correspond to a size of surfaces of the adjusting engagement, such as having surfaces that match surfaces of a flange of a grommet.

Figure 8A:
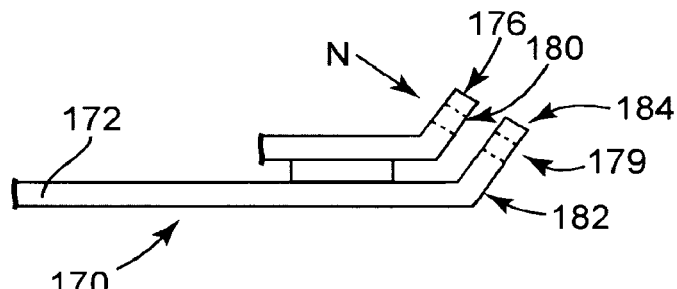
Figure 8B:
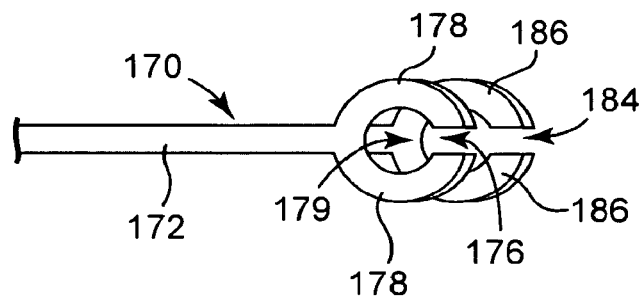

Another embodiment of adjusting tool is shown at FIGS. 8A and 8B. This embodiment of adjusting tool 170 includes features of tool 170 as illustrated at FIGS. 7A and 7B, and also includes an optional second set of arms around aperture 179, located in alignment with arms 178. FIGS. 8A and 8B show side and top views of this embodiment of adjusting tool 170. In addition to arms 178, defining features and surfaces as described, this embodiment of tool 170 includes a second set of arms, 184, that are aligned with arms 178 and that define additional length of aperture 179.

Still referring to FIGS. 8A and 8B, optional arms 186 are structured to prevent tissue from becoming lodged inside of an adjusting engagement (e.g. a grommet) during movement of grommet 32 in a direction N along a segment of implant. For instance, when an adjusting tool is used to move a grommet along a segment of mesh implant, within a patient, tissue may come into contact with the mesh or the grommet and (absent arms 186) can tend to be forced into the aperture of the grommet. Arms 186 become located on the side of the grommet that moves into tissue, and deflect and block tissue from entering an aperture of the grommet. Alternately, or additionally, second arms 186 can be used to move a two-way grommet in a direction opposite of the direction of movement provided by arms 178; i.e., this embodiment of an adjusting tool allows for a two-way grommet to be moved in two different directions (distally, and proximally) along an implant segment.

Figure 10A:
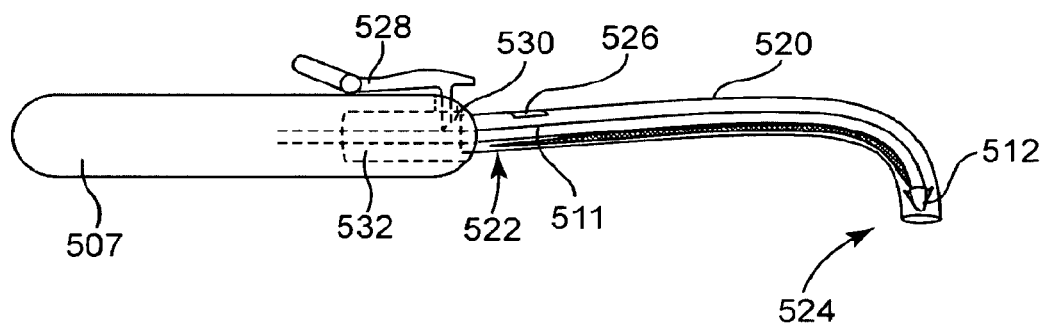
FIGS. 10A and 10B illustrate side, cut-away views of an example of an insertion tool as described.

In use, slots 176 and 184 at distal end 174 can be slid over a segment of implant to place a segment of implant at a location within aperture 179 (defined by and between sets of arms 178 and 186). FIG. 10A shows that bottom surfaces 182 of arms 186 can deflect and block tissue from entering an aperture of adjusting engagement 192, which may be, e.g., a one-way or a two-way grommet used to adjust the location of implant portion 190 relative to implant segment 198, which includes tissue fastener 196 placed within tissue 194.

In use, embodiments of implants as described can be implanted according to methods that include placement of a tissue support portion of an implant at a location to support pelvic tissue, and placement of a tissue fastener attached to an extension portion of an implant (e.g., an extension portion piece), including optional use of an insertion tool that includes a sheath as described. A method may include steps such as engaging a tissue fastener with the distal shaft end, placing a sheath over the shaft and engaged tissue fastener, and inserting the shaft and engaged tissue fastener into a patient with the sheath placed over the shaft in the covered configuration. The sheath may engage an optional mechanical stop to maintain the position of the sheath in the covered configuration. The mechanical stop may be removed to allow the sheath to move (e.g., slide in a proximal direction along the shaft) to an uncovered configuration that uncovers the tissue fastener. The tissue fastener can then be fastened to tissue of a patient, e.g., soft tissue of a pelvic region. If the tissue fastener is a self-fixating tip, the self-fixating tip can be fastened to the soft tissue by using the handle and shaft to push the self-fixating to into the soft tissue. If the tissue fastener fastens to tissue by another mechanism, such as by mechanical grasping, optionally using a shaft that opens or closes a grasping mechanism of the tissue fastener, then the tissue fastener can be caused to engage tissue by manipulation of an actuator or other actuating mechanism to secure the tissue fastener to tissue.

One or more extension portions and optional scaffold portions are placed (by use of an insertion tool with a sheath, or otherwise) for use in supporting the tissue support portion. For example, a tissue fastener at a distal end of an extension portion can be placed at internal tissue of the pelvic region such as muscle, ligament, tendon, fascia, bone, etc. Alternately, an extension portion may include a connector, for connecting to a tool that pulls the connector and extension portion through a tissue path leading to an external incision (e.g., at an external perirectal region, or through an obturator foramen and to an external incision at an inner thigh). As yet another alternative, an extension portion may not include a connector or a self-fixating tip but may be connected to tissue or led through a tissue path internal to the patient, or may be passed through a tissue path and an external incision. Optionally, a tissue fastener at a distal end of a scaffold portion can be connected to internal tissue of the pelvic region such as muscle, ligament, tendon, fascia, bone, etc. Alternately or additionally, an end of a scaffold portion can also be attached to a tissue support portion or an extension portion of an implant. An extension portion or a support portion piece can be attached to the scaffold portion at a location between the ends of the scaffold portion.

Embodiments of methods can be performed using a medial incision such as through a vaginal incision (for female anatomy) or perineal incision (for male anatomy), and by use of an insertion tool (e.g., any insertion tool described herein) that engages a distal end of the extension portion (such as by engaging a tissue fastener) and passes the distal end to a desired location within a pelvic region of a patient.

An end of an extension portion or scaffold portion can be attached to any desired tissue of the pelvic region, or passed through a desired tissue path to an external incision. To attach a distal end of an extension portion or scaffold portion to tissue, a tissue fastener can be attached at the end of the extension or scaffold portion. During installation of the implant, the tissue fastener can be attached to any desired tissue, for example soft tissue such as a muscle (e.g., of the obturator foramen, obturator internus, obturator externus, levator ani, coccygeous, iliococcygeous); ligament such as the sacrospinous ligament or surrounding tissue; tendon such as the arcus tendineus or surrounding tissue (e.g., a region of the arcus tendineus, see WO 2007/016083, published Feb. 8, 2007, and entitled "Methods and Symptoms for Treatment of Prolapse," the entirety of which is incorporated herein by reference); including tissue at or near an ischial spine, e.g., at a region of an ischial spine.

Figure 9:
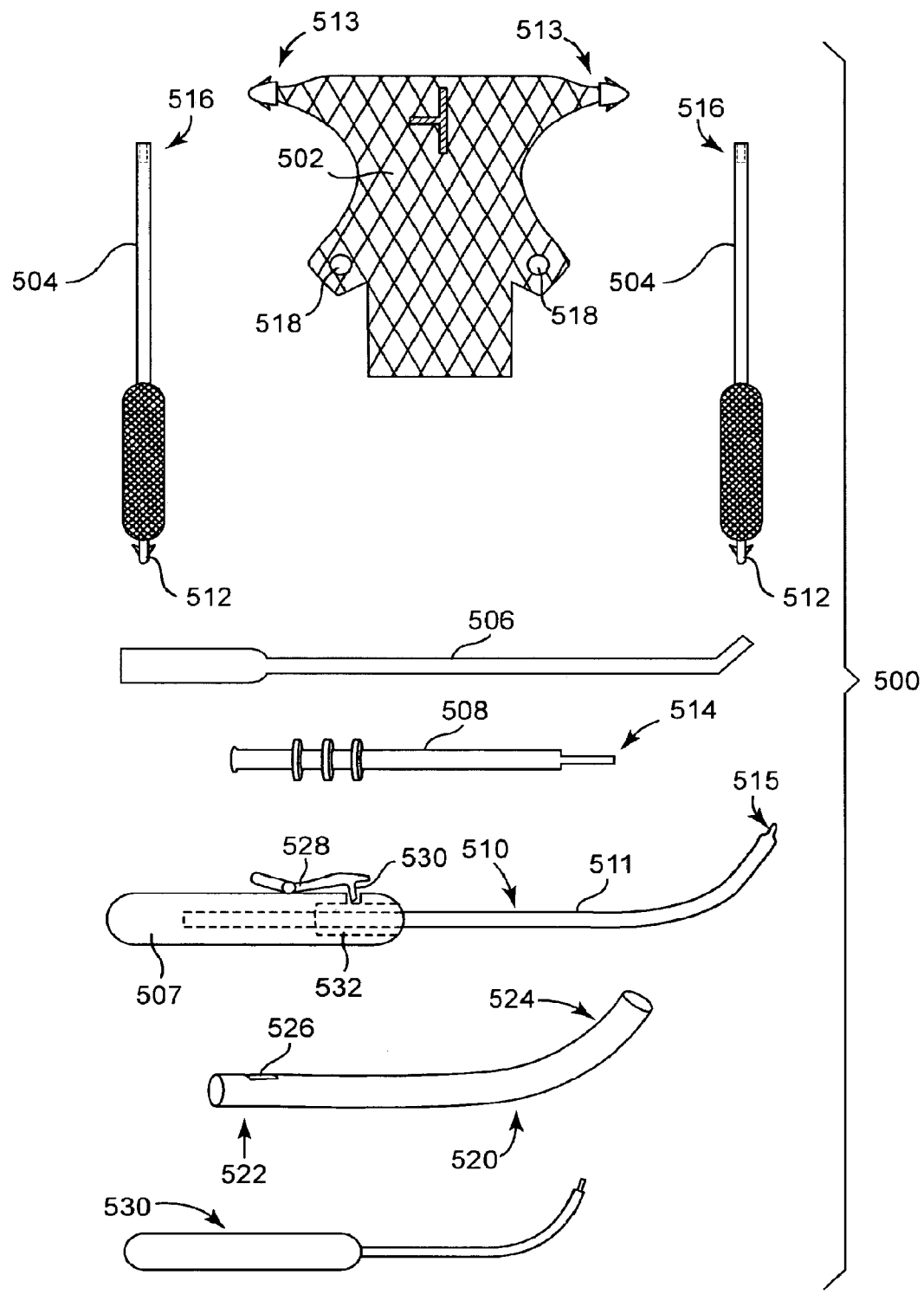
FIG. 9 illustrates an exemplary kit, as described.

The described implants and tools can be combined into kits (e.g., "systems") that contain multiple different combinations of implant, implant pieces, insertion tools, and other tools as described herein. Any of the implants can be in a kit with insertion tools, extension portion pieces, support portion pieces, adjusting tools, grommet management tools, and tissue fasteners, in any combination. FIG. 9 illustrates such combinations. Kit 500 includes support portion piece 502, two extension portion pieces 504 (each shown to have a mesh portion and a non-mesh portion), sheath 520 for use with insertion tool 510, insertion tool 530, optional adjusting tool 506, and optional grommet management tool 508.

Sheath 520 is in the form of a self-supporting polymeric (e.g., polypropylene) tube having proximal end 522, distal end 524, and sidewall aperture 526. Insertion tool 510 can be as described, e.g., as illustrated at FIGS. 1A, 1B, 1C, 1D, 2A, and 2B. As illustrated, insertion tool 510 includes handle 507, including recess 532, and lever 528 including pin (mechanical stop) 530. A distal end of shaft 511 of insertion tool 510 engages tissue fasteners 512, of extension portion pieces 504, e.g., for placing tissue fasteners 512 at a posterior location of a pelvic region such as at a sacrospinous ligament. Aperture 526 of sheath 520 engages pin 530 when sheath 520 covers shaft 511 in a covered engagement, wherein proximal end 522 partially enters recess 532. In an uncovered engagement, proximal end 522 extends further into recess 532 to uncover the distal end of shaft 511.

Extension portion pieces 504 include a mesh-portion and a non-mesh portion, but entirely mesh extension portion pieces could be used. Optional adjusting tool 506 can be as described, e.g., as illustrated at FIGS. 7A and 7B, or 8A and 8B. Optional grommet management tool 508 can be as described, e.g., as illustrated at FIG. 6A or 6B. End 514 of grommet management tool 508 can matingly engage ends 516 of non-mesh portions of extension portion pieces 504, such as at cylindrical bores (shown in shadow).

Insertion tool 530 includes a handle and a shaft, the distal end of the shaft being capable of engaging tissue fasteners 513 of implant support portion piece 502, to allow insertion tool 530 to place tissue fasteners 513 transvaginally, at an anterior location of the pelvic region, e.g., each at an opposite location of an obturator foramen.

Support portion piece 502 can be designed to support posterior vaginal tissue, anterior vaginal tissue, vaginal vault tissue, or another pelvic tissue, and can include optional features such as additional extension portions or scaffold portions or additional adjusting engagements (not shown). For example support portion piece 502 can comprise a support portion piece or implant as described or illustrated herein. Apertures 518 can be one-way adjusting engagements or two-way adjusting engagements.

In use, insertion tool, 510, extension portion piece 504, and sheath 520, can be used by initially placing tissue fastener 512 in contact with distal end 515 of tool 510. As shown at FIG. 10A, sheath 520 can then be placed over shaft 511 and extension portion piece 504 (each is within sheath 520). Proximal end 522 of sheath 520 contacts pin 530, preventing proximal end 522 from fully entering recess 532 of handle 507. This is the covered configuration, wherein distal end 524 of sheath 520 covers tissue fastener 512 engaged with distal end 515 of shaft 511 of insertion tool 510. The covered configuration can be used for inserting a tool, with engaged tissue fastener and extension portion (e.g., extension portion piece), into a patient, e.g., through a transvaginal or other incision, to place tissue fastener 512 at a location in the body near a fixation site.

Figure 10B:
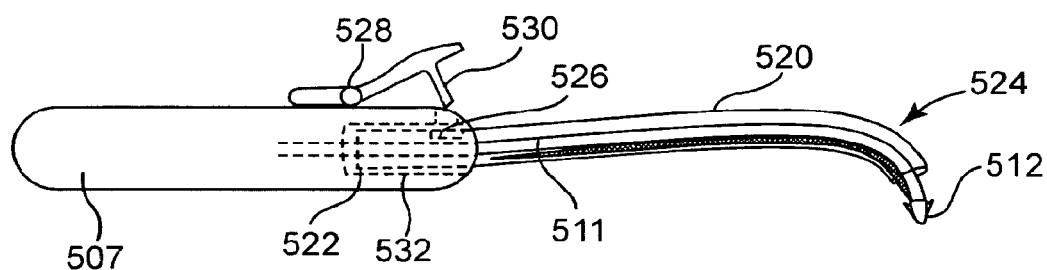

Once near a fixation site the tool and sheath can be converted to the uncovered configuration to allow tissue fastener 512 to engage tissue. FIG. 10B illustrates the uncovered configuration wherein distal end 524 of sheath 520 does not cover tissue fastener 512 engaged with distal end 515 of shaft 511 of insertion tool 510; pin 530 has been moved from engaging proximal end 522, and proximal end 522 has been moved into recess 532. In this uncovered, tissue fastener 512 can engage tissue at a fixation site.

An example of a method as described herein for treating vaginal prolapse, e.g., anterior or posterior vaginal prolapse (including vaginal vault prolapse), can include placing a tissue support portion at tissue of the anterior or posterior vagina or vaginal vault, and fixing one and optionally two posterior extension portions extending from the tissue support portion to a sacrospinous ligament, then securing two anterior extension portions to opposing obturator foramen. Placement of one or all of the extension portions may be performed using an insertion tool that incorporates the use of a sheath as described herein.

An example of a system according to the present description, including an implant and insertion tool for treating vaginal prolapse, can be as follows.

The system can be used to treat or repair vaginal prolapse without external needle passes, by use of a single, transvaginal incision. One embodiment of this type of system can be useful to treat posterior vaginal prolapse by placement of extension portions of an implant at locations that include a sacrospinous ligament, a coccygeus muscle, or both. The implant can be implanted, fixated, and adjusted, as desired, transvaginally, via a single vaginal incision. Unlike other similar systems and methods this described embodiment can be implanted in the body without external trans-gluteal needle passes and is, thus, less invasive.

The system generally includes fixation arms (extension portion pieces) (e.g., as illustrated at FIG. 5B, a center graft (a support portion piece) (e.g., as illustrated at FIG. 4), a delivery device (insertion tool) (e.g., as illustrated at FIG. 1A, 1B, 1C, 1D, 2A, or 2B), and adjusting engagements. These tools and implant pieces can be part of a system as shown at FIG. 9.

A fixation arm can fixate to an internal fixation site, guide the center graft within the body, and aid in internal adjustment of the center graft. Each fixation arm generally includes a stem (non-mesh portion), a mesh segment (mesh portion), and a fixation element (tissue fastener). Components of a fixation arm can be made of polypropylene or any material now known to or yet developed by a person skilled in the art.

FIG. 5B shows an example of a fixation arm that includes a solid polymeric stem (102). A distal end of stem 102 can be over-molded on an end (proximal end) of mesh segment 104. Alternately, stem 102 and mesh segment 104 can be made of a single piece of polymeric material. A fixation element (106) can be over-molded on another (distal) end or portion of mesh segment 104. A proximal end of the stem (109) can be used by a physician during surgery to guide placement of and manipulate, relative to each other: loose eyelet (e.g., a one-way adjusting grommet) of the center graft, the locking eyelet holder (e.g., a grommet management tool), the locking eyelets (e.g., one-way adjusting grommet), and the accessory tool (adjusting tool). The stem can allow the loose eyelets of the center graft and the locking eyelets to be transferred into the body of a patient without encountering tissue-catching issues; e.g., a stem may extend from an incision after placement of a fixation arm, and the stem may be threaded through the loose eyelet outside of the body and away from the confined surgical site. The mesh segment (mesh portion) of the fixation arm can allow free passage of a loose eyelet while permitting at least one locking eyelet to move in one direction to secure the loose eyelet in place. The fixation element can allow strong acute fixation in the sacrospinous ligament or any other soft tissue.

The center graft generally comprises a graft portion (e.g., mesh or biologic material) and optional loose eyelets. The graft portion can be made of extra-light polypropylene (ELPP), a porcine graft, any material now known to or yet developed by a person skilled in the art for use in biological implants, or combinations of materials. One loose eyelet can be over-molded on a side of the graft portion and another loose eyelet can be over-molded on another or opposite side of the graft portion. The loose eyelets can be used to allow a physician to translate the center graft into and out of the body for proper positioning. In one embodiment, the positioning and repositioning of the center graft is accomplished on the stem prior to being secured with the locking eyelets.

According to this or other implants, implant pieces, or systems, portions of the mesh arms (e.g., extension portions) can have one or more rolls or folds disposed along a length thereof that are sutured prior to system implantation and held together, e.g., by sutures, staples, adhesive, or another fastener. If the implant is too tight, a physician or other medical staff can cut the sutures holding the rolls or folds together in vivo to increase a length of one or more of the mesh arms. The increased length loosens the center graft.

The locking system (adjusting mechanism) generally includes the locking eyelets (e.g., one-way adjusting grommets), an optional locking eyelet holder (grommet management tool), loose eyelets (e.g., two-way adjusting grommets), and an optional accessory tool (e.g., adjusting tool). All components of the locking system can be made of polypropylene, or any material now known to or yet developed by a person skilled in the art. The locking eyelet can be a one-way tensioning device that, once engaged with the mesh segment of the fixation arm, permits only increased tensioning of the center graft.

The locking eyelet can associate with a loose eyelet of the center graft to fixate the center graft on the mesh segment of the fixation arm. The locking eyelet can feature generally inwardly radiating teeth that can be oriented at an angle to allow translation along the fixation arm in one or both directions along the stem of the fixation arm and to prevent translation in a direction toward the stem of the fixation arm once engaged with the mesh segment (e.g., mesh portion). The locking eyelet holder, capable of being manipulated by a physician or other medical staff, keeps the locking eyelets correctly oriented and can mate with an end of the fixation arm to translate the locking eyelets when necessary. Loose eyelets can be over-molded on the center graft. Each loose eyelet can be loaded on the proximal end of the stem of the fixation arm and can be translated on the fixation arm for proper positioning of the center graft. The accessory tool can aide a physician or other medical staff when translating the loose eyelets of the center graft and the locking eyelets on the fixation arm. The accessory tool can be especially helpful in small body cavities or hard-to-reach locations within a patient, such as but not necessarily in a pelvic region.

The delivery device (insertion tool) generally includes a shaft such as a solid needle, and a handle. The needle generally comprises a solid length of shaft and a tip at the distal end, wherein the tip engages a fixation element (e.g., tissue fastener, such as a self-fixating tip). The needle can transport the fixation element of the fixation arm to a desired fixation site (e.g., at soft tissue of a pelvic region) and can perform placement of the fixation element in soft tissue or tissue selected by the physician or other medical staff.

The following can be a method of implantation of the above system, for treating vaginal prolapse. This method can be performed with an insertion tool that involves a sheath as described, or without a sheath:

1. Determine vaginal apex and each lateral uterosacral dimple point.
2. Use preferred incision method through posterior vaginal wall. Use full thickness dissection through recto-vaginal fascia. Leave approximately 2 cm of vaginal wall distal to apex intact for attachment.
3. Dissect toward the ischial spine and palpate the ischial spine with the index finger.
4. Begin blunt dissection in the medial direction along the sacrospinous ligament. Dissect 2-3 finger breadths towards the sacrum.
5. Perform steps 3-4 for contralateral side.
6. Insert a fixation element of a fixation arm onto a needle tip of a delivery device.
7. Grasp handle of delivery device with left hand.
8. To locate area of fixation of patient right, palpate the sacrospinous ligament two-finger breadths medially from the ischial spine (at least 2 cm medially from the ischial spine).
9. Insert both the index and middle finger into the vaginal cavity.
10. Place first bend of needle at fixation point and at the tip of the middle finger.
11. Drive the fixation element into the ligament until the needle tip is inserted up to the first bend.
12. Remove needle tip from the fixation element by placing finger at area of implantation and pulling back gently on needle shaft until it disengages from fixation element.
13. Carefully remove the delivery device though incision and out introitus.
14. For patient left, perform steps 6-13, switching to opposite side for all directional instructions.
15. Determine the correct orientation of the center graft. Locate loose eyelets on the center graft. Slide the stem of one of the fixation arms exiting from the introitus through its corresponding loose eyelet of the center graft. Slide the stem of the other fixation arm exiting from the introitus through its corresponding loose eyelet of the center graft.
16. Load the accessory tool on the proximal end of the stem of one of the fixation arms.
17. Translate the accessory tool a short distance on the fixation arm toward the fixation site. By this action the center graft will be pushed into the pelvic cavity. Remove the accessory tool from the fixation arm.
18. Repeat steps 16-17 for the other fixation arm.
19. Repeat steps 16-18 until desired position of the center graft has been achieved. To loosen the center graft, grab the center graft and pull towards the introitus.
20. Once adjustment of the center graft is final, locate the locking eyelet holder. Align and engage the end of the holder onto the proximal end of a stem of one of the fixation arms. Load one locking eyelet on the fixation arm and disengage the locking eyelet holder.
21. Repeat step 20 to load one locking eyelet on the other fixation arm.
22. Reload accessory tool on proximal end of the stem of one of the fixation arms. Proceed to translate accessory tool on fixation arm toward fixation site until locking eyelet reaches the loose eyelet on the center graft. Palpate to verify locking eyelet rests against surface of center graft. If not, readjust with accessory tool. Note: in at least one embodiment of the described methods (if locking eyelet is a one-way adjusting grommet) a locking eyelet cannot be reversed once its teeth come into contact with a portion of the mesh segment that is proximal fixation arm.
23. Repeat step 22 for other fixation arm.
24. Trim mesh segment at least 1 cm proximal to the locking eyelet. Verify that discarded stems contain mesh on its distal end. If not, trim away remaining stem from the mesh segment in vivo.
25. Continue with repair of posterior defects, if needed. Avoid placing any tension while suturing the mesh. Close recto vaginal fascia over the mesh and close vaginal incision.

Embodiment of methods that incorporate these steps can treat cystocele, rectocele, enterocele, vault prolapse, and/or any pelvic dysfunction relating to rectal, vaginal, or bladder issues.

Embodiments of fixation elements can be over-molded on the free end of each mesh arm. The fixation element can have a bore to receive the needle of a delivery device. During a surgical procedure, the fixation element or the needle can dilate the tissue. The fixation element can then be attached at a location at a posterior pelvic region, such as any of a: sacrospinous ligament, coccygeus muscle, iliococcygeus muscle, arcus tendineus (white line), fascia at the ischial spine, puborectalis muscle, piriformis muscle, fascia at the obturator canal, or any location on the levator ani. Other fixation sites are also considered to be within the spirit and scope of the invention and the above list should not be considered limiting.

Embodiments of delivery devices (insertion tools) can generally include a shaft (e.g., a solid needles shaft), a handle, and a distal tip at the end of the shaft that engages a fixation element. The needle can provide transport of the fixation element of the center graft to the target fixation site and can perform placement of the fixation element in tissue. The needle can have many possible shapes, depending where the fixation element is intended to fixate. For example, three-dimensionally curved helical-shaped needles can be used near the white line. Two-dimensionally curved sickle-shaped needles can be used near the sacrospinous ligament area. In one embodiment, the needle can have a sliding component that pushes the needle and the fixation element into the tissue. The sliding component can be a needle-sub-needle combination with the sub-needle having a smaller diameter cross-section than the needle. The sub-needle can be disposed in a cavity in the needle or it can be disposed adjacent to and travel generally parallel with a longitudinal axis of the needle. An actuator can be disposed on the needle to move the sub-needle between a retracted position and an extended position, with the extended position being used for placement of the fixation element.

The sliding component can also be disposed on a finger tool as well. In one embodiment, the finger tool includes a receptacle having a shape adapted to receive a finger or thumb of a physician. A needle or upright member having enough rigidity for successful placement of the fixation element can be disposed to and extend generally away from the receptacle. The fixation element can then be disposed on (engage) a free end of the upright member (e.g., needle). The upright member can having any size and shape necessary for fixating the fixation element into the tissue. For example, the upright member can be generally straight, curved, hooked, or angled.

In particular embodiments, the system can include support of the apical portion of the vagina. The inferior aspect of the center graft can fixate at the sacrospinous ligament. The shape of the center graft can be modified to accommodate the new fixation site and to optimize structural support of the anterior vaginal compartment.

Another embodiment of a system generally can include a center graft, fixating arms, a delivery system (insertion tool) including a sheath, a latch-and-release mechanism for engaging the sheath with the insertion tool, and optional accessory tool or grommet management tool.

Edges of a center graft can be made of any material now known to or yet developed by a person skilled in the art. Edges of the center graft can be curved to reduce curling under tension. The shape of the center graft can be tailored for centering and orientation. The center graft generally comprises a superior aspect (sometimes referred to as an anterior portion), an inferior aspect (sometimes referred to as a posterior portion), and optionally a graft tail. The superior aspect can fixate through extension portions at the obturator internus muscle. The superior aspect can include fixation elements, one on each side. The inferior aspect can fixate through extension portions at or near the sacrospinous ligament. Although generally specific fixation sites are noted, those skilled in the art realize that other fixation sites are also possible and should be considered within the spirit and scope of the invention. The inferior aspect can preferably include locking eyelets, one on each side. The locking eyelet can associate with a loose eyelet of the center graft to fixate the center graft on the mesh segment of the fixation arm. The locking eyelet can feature teeth that can be oriented at an angle to allow translation along the fixation arm and to prevent translation in the opposite direction once engaged with the mesh segment of the fixation arm. The graft tail can be trimmed without negatively affecting its load-bearing portion. The angle of the inferior attachment tab can approximate the angle between the mesh orientation and the sacrospinous ligament attachment point.

The delivery system generally comprises an inferior delivery device (insertion tool) and a superior delivery device (insertion tool). The inferior delivery device generally comprises a needle, a sheath, a handle, and optional a latching-and-release mechanism (e.g., as does tool 510, with shaft 520, of FIG. 9). The needle is used to transport and fixate the fixation element of a fixation arm to the sacrospinous ligament or any other desired fixation site. A superior delivery device may include a sheath, or may include a needle without a sheath (as does tool 530 of FIG. 9.

A sheath can perform at least three functions. First, a sheath can shield the fixation arm (including the tissue fastener) during delivery to minimize the possible inconvenience of the fixation element (tissue fastener) falling off or the fixation element getting caught on tissue. Second, a sheath can protect the physician's glove and finger from snagging on the fixation element during delivery. Third, a sheath can provide a hard stop against over-insertion of the fixation element into the tissue.

The handle of an insertion tool adapted for use in conjunction with a sheath can feature a latch-and-release mechanism, which includes a mechanical stop, to hold the sheath secure to the handle of the inferior delivery device and to prevent premature exposure of the fixation element during deployment deep inside the pelvis. The latch-and-release mechanism releases the sheath prior to fixation element insertion into soft tissue (e.g., sacrospinous ligament, coccygeus muscle, levator ani muscle, obturator foramen, etc.). A sheath in conjunction with a latch- and release mechanism (and optional handle recess) can also control the depth of fixation element insertion into soft tissue. The latch-and-release mechanism can be a lever generally comprising a rigid bar and a fulcrum. (Other options located on an insertion tool handle, shaft, or elsewhere, are also possible, as will be appreciated.) The rigid bar can feature a thumb-engaging portion and a sheath engaging portion (e.g., mechanical stop, pin, or "trigger-latch") at opposite ends from one another. At rest, the sheath-engaging portion engages or abuts with the sheath to hold the sheath secure to the handle. When the thumb-engaging portion is depressed, the rigid bar can pivot on the fulcrum causing the sheath-engaging portion to disengage with the sheath.

An example of an inferior delivery needle, including a sheath, can include one or more features such as: a leading edge of trigger latch is angled, allowing the sheath to raise the trigger latch as the sheath presses against the trigger latch during a locking procedure; when the sheath reaches a desired locking position, the latch drops down to engage an aperture in a sidewall at a proximal end of the sheath, restricting the sheath from moving forward or backward; depth limiting stop (e.g., a length of a recess in a handle) limits the sheath from retracting too far into the handle, thus limiting the length of needle tip exposed past the sheath and inserted into the tissue; the distance from the latch stop to the depth limiting stop (e.g., approximately distance d of FIGS. 1A and 1B) is the desired depth limiting distance.

A superior insertion tool can include a needle (such as a solid metal needle) and preferably a handle; the superior insertion tool can optionally include a sheath. The needle can be used to transport and fixate the fixation elements of the center graft to the obturator internus muscle. The needle can be curved to allow for direct approach to the muscle. The needle can feature a flat surface on its tip that corresponds to a surface of a fixation element, to prevent rotation of the fixation element and to control orientation of the fixation element (e.g., and tines or extension portions of the fixation element) with respect to the muscle fiber.

The following can be a method of implantation of the above system, including an inferior insertion tool that works in conjunction with a sheath, and a superior insertion tool that does not require a sheath:

1. Load a fixation element of the center graft onto the needle tip of the superior delivery device (e.g., a fixation element 513 of an implant, and delivery device 530, illustrated at FIG. 9).

2. Aim the needle toward the obturator internus muscle.

3. Track the needle along the posterior surface of the ischiopubic ramus in an arching motion.

4. Continue to advance the fixation element in an arching motion until the obturator internus muscle is penetrated by the fixation element.

5. Repeat steps 1-4 for contra-lateral side.

6. Load the fixation element of a fixation arm (e.g., 504 of FIG. 9) onto the needle tip of the inferior delivery device (e.g., 510 of FIG. 9).

7. Insert the needle and engaged fixation element into the proximal end of the sheath (e.g., sheath 520 of FIG. 9).

8. Slide the sheath over the needle and fixation arm, making sure not to dislodge the fixation element by inserting the distal needle end and engaged mesh arm into a proximal end of the sheath. Slide the sheath down the needle until a proximal end of the sheath engages with the latch-and-release mechanism on the handle. Verify the sheath is secure and the needle tip does not protrude from the distal end of the sheath.

9. Locate the sacrospinous ligament by palpation.

10. While keeping the index finger on the ligament, guide the sheath tip along and lateral to the finger, toward the sacrospinous ligament.

11. Place the tip of the sheath to contact the sacrospinous ligament. Release the latch-and-release mechanism and allow the sheath to slide into the recess, toward the handle, to uncover the fixation element (i.e., take the uncovered configuration). Keeping the trigger depressed, drive the fixation element into the ligament. The sheath will prohibit the needle from getting too deep into the ligament.

12. Remove the needle and sheath from the area of implantation by pulling back gently on the needle until the needle disengages the fixation element. Carefully remove the needle assembly through the incision and out of the introitus. If the sheath does not retract with the needle, gently remove the sheath through the incision and out of the introitus.

13. Repeat steps 6-13 for contra-lateral side.

14. Locate one-way adjusting eyelets on the graft. Slide each eyelet over the stem of a corresponding fixation arm exiting from the introitus. (These steps involve an implant piece that includes one-way adjusting eyelets; optionally, a two-way adjusting eyelet may be placed on an implant piece, held in place with a one-way adjusting eyelet, as described elsewhere herein.)

15. Load the accessory tool on the proximal end of the stem of one of the fixation arms.

16. Translate the accessory tool a short distance on the fixation arm toward the fixation site. By this action, center graft will be pushed into pelvic cavity. Remove the accessory tool from the fixation arm.

17. Repeat steps 15-16 for the other fixation arm.

18. Repeat steps 15-17 until desired position of the center graft has been achieved.

19. Trim mesh segment at least 1 cm proximal to the locking eyelet. Verify that discarded stems contain mesh on its distal end. If not, trim away remaining stem from the mesh segment in vivo.

Various embodiments disclosed herein can be combined with neuromuscular stimulation to treat pelvic prolapse and any pain/discomfort associated with it or post-cancer or other reconstructive surgery.

The invention claimed is:

1. A combination surgical insertion tool and pelvic implant, the tool comprising
 a handle,
 a shaft comprising a proximal shaft end attached to the handle, and a distal shaft end,
 a sheath that is alternately removable from the shaft and engageable with the shaft and that can be placed over the shaft to engage the shaft and allow at least two configurations: a covered configuration in which the sheath covers the distal shaft end, and an uncovered configuration in which the sheath covers a portion of the shaft and does not cover the distal shaft end,
 the pelvic implant comprising:
  a support portion piece,
  an extension portion piece, and
  a tissue fastener at a distal end of the extension portion piece, the tissue fastener being capable of engaging the distal shaft end,
 wherein the distal shaft end is configured to engage the tissue fastener in a manner by which the insertion tool is capable of pushing the tissue fastener into tissue,
  wherein with the tissue fastener engaging the distal shaft end, the sheath can be placed over the shaft and the extension portion, and when the tissue fastener engages the distal end of the shaft, the sheath can fit over the shaft and the extension portion and can be moved between the covered configuration and the uncovered configuration, and
  the sheath covers the tissue fastener when the sheath is in the covered configuration and the sheath does not cover the tissue fastener when the sheath is in the uncovered configuration.

2. A combination as recited at claim 1, wherein the implant comprises
 a set of two superior extension portions extending from the support portion piece, and a set of two inferior extension portions extending from the support portion piece,
 wherein, when the support portion piece is placed to support tissue of a vagina, each superior extension portion can be connected to tissue of an opposing obturator foramen, and each inferior extension portion can be connected to sacrospinous ligament.

3. A combination as recited at claim 1, comprising one or more of a grommet management tool and an adjusting tool.

4. A combination as recited at claim 1, wherein
 the tool is adapted to engage the tissue fastener and to place the tissue fastener transvaginally at a sacrospinous ligament,
 the combination further comprising a second insertion tool adapted to place the tissue fastener transvaginally at an obturator foramen.

5. The combination according to claim 1 wherein the extension portion piece comprises a mesh portion and a non-mesh portion.

6. The combination of claim 5 wherein the tissue fastener is located at an end of the mesh portion.

7. The combination of claim 5 wherein the support portion piece comprises an adjusting engagement for adjustably engaging the extension portion piece.

8. The combination of claim 7 wherein the support portion piece further comprises two additional tissue fasteners.

9. A method of implanting an implant in a patient, the method comprising
providing a combination comprising a surgical insertion tool and pelvic implant, the tool comprising
a handle,
a shaft comprising a proximal shaft end attached to the handle, and a distal shaft end,
a sheath that is alternately removable from the shaft and engageable with the shaft and that can be placed over the shaft to engage the shaft and allow at least two configurations: a covered configuration in which the sheath covers the distal shaft end, and an uncovered configuration in which the sheath covers a portion of the shaft and does not cover the distal shaft end,
the pelvic implant comprising:
a support portion piece,
an extension portion piece, and
a tissue fastener at a distal end of the extension portion piece, the tissue fastener being capable of engaging the distal shaft end,
wherein the distal shaft end is configured to engage the tissue fastener in a manner by which the insertion tool is capable of pushing the tissue fastener into tissue,
engaging the tissue fastener with the distal shaft end,
placing the sheath over the shaft, the extension portion piece, and the engaged tissue fastener with the sheath in a covered configuration that covers the distal shaft end and engaged tissue fastener,
inserting the shaft and engaged tissue fastener into a patient, with the sheath placed over the shaft in the covered configuration,
moving the sheath to an uncovered configuration that uncovers the tissue fastener, and
fastening the tissue fastener to tissue.

10. The method of claim 9 comprising inserting the tissue fastener into soft tissue selected from sacrospinous ligament and coccygeus muscle.

11. The method of claim 10 wherein the implant comprises
a set of two superior extension portions extending from the support portion piece, and a set of two inferior extension portions extending from the support portion piece,
the method comprising placing the support portion piece to support tissue of a vagina,
fixing each superior extension portion to tissue of an opposing obturator foramen,
fixing each inferior extension portion to soft tissue of sacrospinous ligament or coccygeus muscle.

12. The method of claim 9 wherein the extension portion piece comprises a mesh portion and a non-mesh portion, the tissue fastener at an end of the mesh portion.

13. A method of implanting an implant in a patient, the method comprising
providing a surgical insertion tool useful for implanting a pelvic implant, the tool comprising
a handle,
a shaft comprising a proximal shaft end attached to the handle, and a distal shaft end, and
a sheath that is alternatively removable from the shaft and engageable with the shaft and that can be placed over the shaft to engage the shaft and allow at least two configurations: a covered configuration in which the sheath covers the distal shaft end, and an uncovered configuration in which the sheath covers a portion of the shaft and does not cover the distal shaft end, and
the implant comprising a tissue support portion, an extension portion comprising the tissue fastener at a distal shaft end,
engaging the tissue fastener with the distal shaft end,
placing the sheath over the shaft, the extension portion, and the engaged tissue fastener with the sheath in a covered configuration that covers the distal shaft end and engaged tissue fastener,
inserting the shaft and engaged tissue fastener into a patient, with the sheath placed over the shaft in the covered configuration,
moving the sheath to an uncovered configuration that uncovers the tissue fastener, and
fastening the tissue fastener to tissue.

14. The method of claim 13 comprising inserting the tissue fastener into soft tissue selected from sacrospinous ligament and coccygeus muscle.

15. The method of claim 14 wherein the implant comprises
a set of two superior extension portions extending from the tissue support portion, and a set of two inferior extension portions extending from the tissue support portion,
the method comprising placing the tissue support portion to support tissue of a vagina,
fixing each superior extension portion to tissue of an opposing obturator foramen,
fixing each inferior extension portion to soft tissue of sacrospinous ligament or coccygeus muscle.

16. The method of claim 13 wherein the extension portion comprises an extension portion piece comprising a mesh portion and a non-mesh portion, the tissue fastener at an end of the mesh portion.

* * * * *